United States Patent
Savastano et al.

(10) Patent No.: US 11,224,458 B2
(45) Date of Patent: Jan. 18, 2022

(54) HYDRODYNAMIC VORTEX ASPIRATION CATHETER

(71) Applicant: THE REGENTS OF THE UNIVERSITY OF MICHIGAN, Ann Arbor, MI (US)

(72) Inventors: Luis Emilio Savastano, Ypsilanti, MI (US); Jeffrey Stephen Plott, Algonac, MI (US); Yang Liu, Ann Arbor, MI (US); Yihao Zheng, Ann Arbor, MI (US); Albert Jau-Min Shih, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 17/027,048

(22) Filed: Sep. 21, 2020

(65) Prior Publication Data

US 2021/0045770 A1 Feb. 18, 2021

Related U.S. Application Data

(63) Continuation-in-part of application No. 16/156,519, filed on Oct. 10, 2018, now Pat. No. 10,960,178, and
(Continued)

(51) Int. Cl.
*A61B 17/3207* (2006.01)
*A61B 17/22* (2006.01)
*A61B 17/00* (2006.01)

(52) U.S. Cl.
CPC ...... *A61B 17/320758* (2013.01); *A61B 17/22* (2013.01); *A61B 2017/00685* (2013.01);
(Continued)

(58) Field of Classification Search
CPC .............. A61B 17/22; A61B 17/221; A61B 17/320758; A61B 17/320725; A61B 17/320783
See application file for complete search history.

(56) References Cited

U.S. PATENT DOCUMENTS 4,646,736 A 3/1987 Auth
5,108,411 A * 4/1992 McKenzie ............... A61B 8/12
604/264
(Continued)

FOREIGN PATENT DOCUMENTS

AU 2013266995 A1 1/2014
EP 2217158 B1 10/2014
(Continued)

OTHER PUBLICATIONS

European Search Report issued in European Application No. 18784090.5 dated Oct. 30, 2020.
(Continued)

*Primary Examiner* — Tuan V Nguyen
(74) *Attorney, Agent, or Firm* — Harness, Dickey & Pierce, P.L.C.

(57) ABSTRACT

An actuated telescoping system for navigation within a vascular lumen and thrombectomy of a thrombus. The system includes a tubular catheter member having an open distal end defining a catheter lumen, a vacuum source, a rotational drive system, a flexible shaft having a channel coupled to the rotational drive system for rotational movement in response thereto, and an optional guidewire selectively inserted at least partially within the flexible shaft. The flexible shaft is at least partially disposed within the tubular catheter member configured for uncoupled rotational and translational motion therein and to optionally define a corkscrew motion in response to rotational driving force by the drive system that results in formation of hydrodynamic
(Continued)

vortices within the catheter lumen. The telescoping system can be capable of reversibly transitioning between navigation and thrombectomy modes by differentially disposing and actuating the components and enable faster, more efficient and simpler removal of thromboembolic material.

30 Claims, 21 Drawing Sheets

Related U.S. Application Data a continuation of application No. PCT/US2019/026737, filed on Apr. 10, 2019, which is a continuation-in-part of application No. 16/156,519, filed on Oct. 10, 2018, now Pat. No. 10,960,178, which is a continuation-in-part of application No. PCT/US2018/026831, filed on Apr. 10, 2018.

(60) Provisional application No. 62/483,580, filed on Apr. 10, 2017.

(52) U.S. Cl.
CPC ............... *A61B 2017/00991* (2013.01); *A61B 2017/22045* (2013.01); *A61B 2017/22079* (2013.01); *A61B 2017/320766* (2013.01); *A61B 2217/005* (2013.01); *A61B 2217/007* (2013.01)

(56) References Cited

U.S. PATENT DOCUMENTS

| | | |
|---|---|---|
| 5,135,482 A | 8/1992 | Neracher |
| 5,423,799 A | 6/1995 | Shiu |
| 5,695,507 A | 12/1997 | Auth et al. |
| 5,876,414 A | 3/1999 | Straub |
| 5,971,996 A | 10/1999 | Tugendreich et al. |
| 6,001,112 A | 12/1999 | Taylor |
| 6,090,118 A | 7/2000 | McGuckin, Jr. |
| 6,113,614 A | 9/2000 | Mears |
| 6,183,450 B1 | 2/2001 | Lois |
| 6,228,046 B1 | 5/2001 | Brisken |
| 6,238,405 B1 | 5/2001 | Findlay, III et al. |
| 6,287,271 B1 | 9/2001 | Dubrul et al. |
| 6,508,782 B1 | 1/2003 | Evans et al. |
| 6,616,676 B2 | 9/2003 | Bashiri et al. |
| 6,676,637 B1 | 1/2004 | Bonnette et al. |
| 6,767,353 B1 | 7/2004 | Shiber |
| 6,926,725 B2 | 8/2005 | Cooke et al. |
| 6,945,977 B2 | 9/2005 | Demarais et al. |
| 7,037,316 B2 | 5/2006 | McGuckin, Jr. et al. |
| 7,399,307 B2 | 7/2008 | Evans et al. |
| 7,507,246 B2 | 3/2009 | McGuckin et al. |
| 7,666,161 B2 | 2/2010 | Nash et al. |
| 7,833,239 B2 | 11/2010 | Nash |
| 7,942,852 B2 | 5/2011 | Mas et al. |
| 7,947,012 B2 | 5/2011 | Spurchise et al. |
| 7,959,608 B2 | 6/2011 | Nash et al. |
| 7,976,528 B2 | 7/2011 | Nash et al. |
| 8,075,510 B2 | 12/2011 | Aklog et al. |
| 8,092,470 B2 | 1/2012 | Miyamoto et al. |
| 8,647,355 B2 | 2/2014 | Escudero et al. |
| 8,734,374 B2 | 5/2014 | Aklog et al. |
| 8,764,779 B2 | 7/2014 | Levine et al. |
| 8,920,402 B2 | 12/2014 | Nash et al. |
| 9,050,127 B2 | 6/2015 | Bonnette et al. |
| 9,282,992 B2 | 3/2016 | Levine et al. |
| 9,463,035 B1 | 10/2016 | Greenhalgh et al. |
| 9,492,192 B2 | 11/2016 | To et al. |
| 9,539,022 B2 | 1/2017 | Bowman |
| 9,808,277 B2 | 11/2017 | Nash et al. |
| 9,848,881 B2 | 12/2017 | Sutton et al. |
| 9,943,321 B2 | 4/2018 | Nita |
| 10,064,645 B2 | 9/2018 | Levine et al. |
| 10,117,671 B2 | 11/2018 | McGuckin, Jr. et al. |
| 10,154,854 B2 | 12/2018 | To et al. |
| 10,183,146 B2 | 1/2019 | Yang et al. |
| 10,183,147 B2 | 1/2019 | Yang et al. |
| 10,188,409 B2 | 1/2019 | Smalling |
| 10,213,582 B2 | 2/2019 | Garrison et al. |
| 10,307,340 B2 | 6/2019 | Bagwell et al. |
| 2002/0138088 A1 | 9/2002 | Nash et al. |
| 2003/0139751 A1 | 7/2003 | Evans et al. |
| 2004/0082962 A1 | 4/2004 | Demarais et al. |
| 2004/0181249 A1* | 9/2004 | Torrance ........ A61B 17/320725 606/170 |
| 2004/0220519 A1 | 11/2004 | Wulfman et al. |
| 2007/0208370 A1 | 9/2007 | Hauser et al. |
| 2007/0219484 A1 | 9/2007 | Straub |
| 2007/0239182 A1 | 10/2007 | Glines et al. |
| 2007/0250096 A1 | 10/2007 | Yamane et al. |
| 2008/0097499 A1 | 4/2008 | Nash et al. |
| 2008/0289181 A1 | 11/2008 | Kozak et al. |
| 2008/0306498 A1 | 12/2008 | Thatcher et al. |
| 2009/0163846 A1 | 6/2009 | Aklog et al. |
| 2009/0171368 A1 | 7/2009 | Pearce et al. |
| 2011/0022075 A1 | 1/2011 | Christiansen et al. |
| 2011/0087147 A1 | 4/2011 | Garrison et al. |
| 2011/0282370 A1 | 11/2011 | Levine et al. |
| 2012/0226093 A1 | 9/2012 | Creighton |
| 2014/0088517 A1 | 3/2014 | Calderone |
| 2014/0148830 A1 | 5/2014 | Bowman |
| 2014/0303658 A1 | 10/2014 | Bonnette et al. |
| 2014/0309672 A1 | 10/2014 | Labropoulos et al. |
| 2015/0094748 A1 | 4/2015 | Nash et al. |
| 2015/0112376 A1 | 4/2015 | Molaei et al. |
| 2016/0089227 A1 | 3/2016 | Loh |
| 2016/0135829 A1 | 5/2016 | Holochwost et al. |
| 2016/0220741 A1 | 8/2016 | Garrison et al. |
| 2017/0027604 A1 | 2/2017 | Wallace |
| 2017/0105743 A1 | 4/2017 | Vale et al. |
| 2017/0238950 A1 | 8/2017 | Yang et al. |
| 2017/0238953 A1 | 8/2017 | Yang et al. |
| 2018/0000510 A1 | 1/2018 | Nash et al. |
| 2018/0207397 A1 | 7/2018 | Look et al. |
| 2018/0242989 A1 | 8/2018 | Nita |
| 2018/0263642 A1 | 9/2018 | Nita |
| 2018/0280043 A1 | 10/2018 | Donegan |
| 2019/0008534 A1 | 1/2019 | Garrison et al. |
| 2019/0038300 A1 | 2/2019 | Savastano et al. |
| 2019/0046218 A1 | 2/2019 | Garrison et al. |

FOREIGN PATENT DOCUMENTS

| | | |
|---|---|---|
| EP | 3141201 A1 | 3/2017 |
| WO | 2000045716 A1 | 8/2000 |
| WO | WO-2015109176 A1 | 7/2015 |
| WO | 2018019829 A1 | 2/2018 |
| WO | 2018215840 A1 | 11/2018 |
| WO | 2019115809 A1 | 6/2019 |

OTHER PUBLICATIONS

International Search Report and Written Opinion of the International Searching Authority issued in PCT/US2018/026831, dated Jul. 26, 2018.

Karthikeshwar et al. "The Use of Mechanical Thrombectomy Devices in the Management of Acute Peripheral Arterial Occlusive Disease" Journal of Vascular and Interventional Radiology, vol. 12, Issue 4, 405-411.

International Search Report and Written Opinion of the International Searching Authority issued in PCT/US20191026737, dated Jul. 30, 2019.

Extended European Search Report dated Oct. 20, 2021 in corresponding European Application No. 19785481.3.

\* cited by examiner

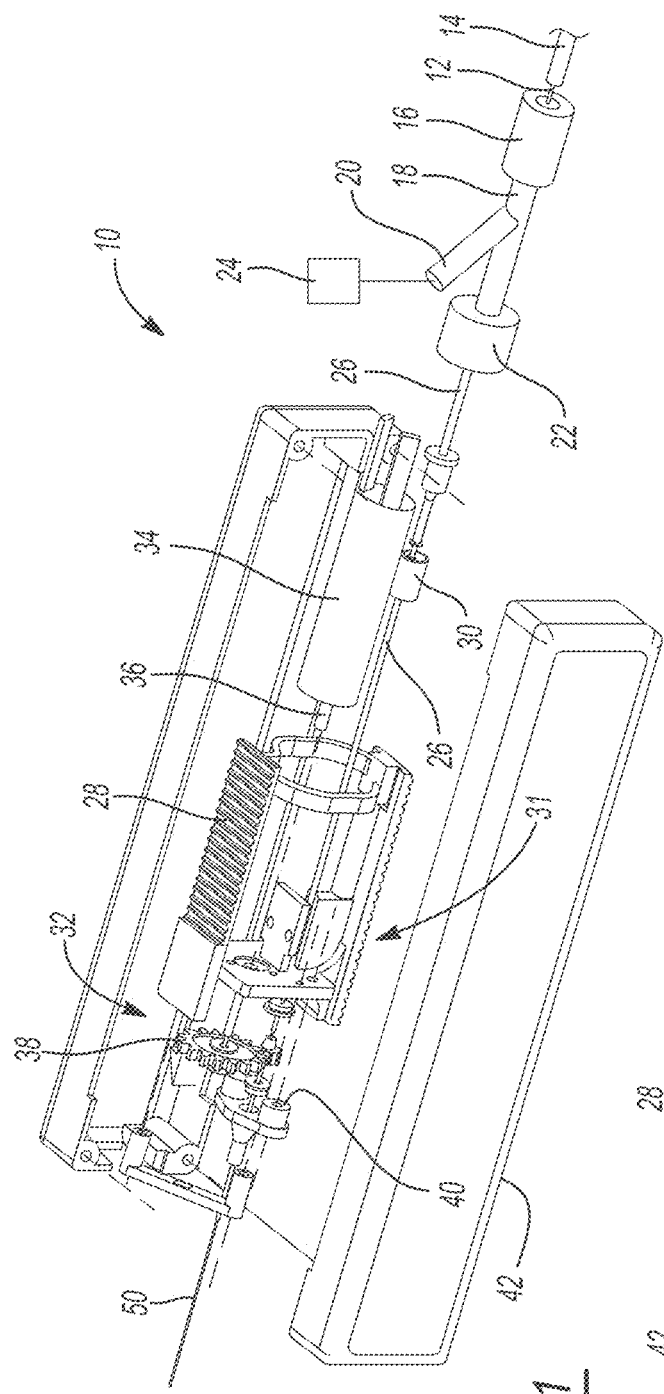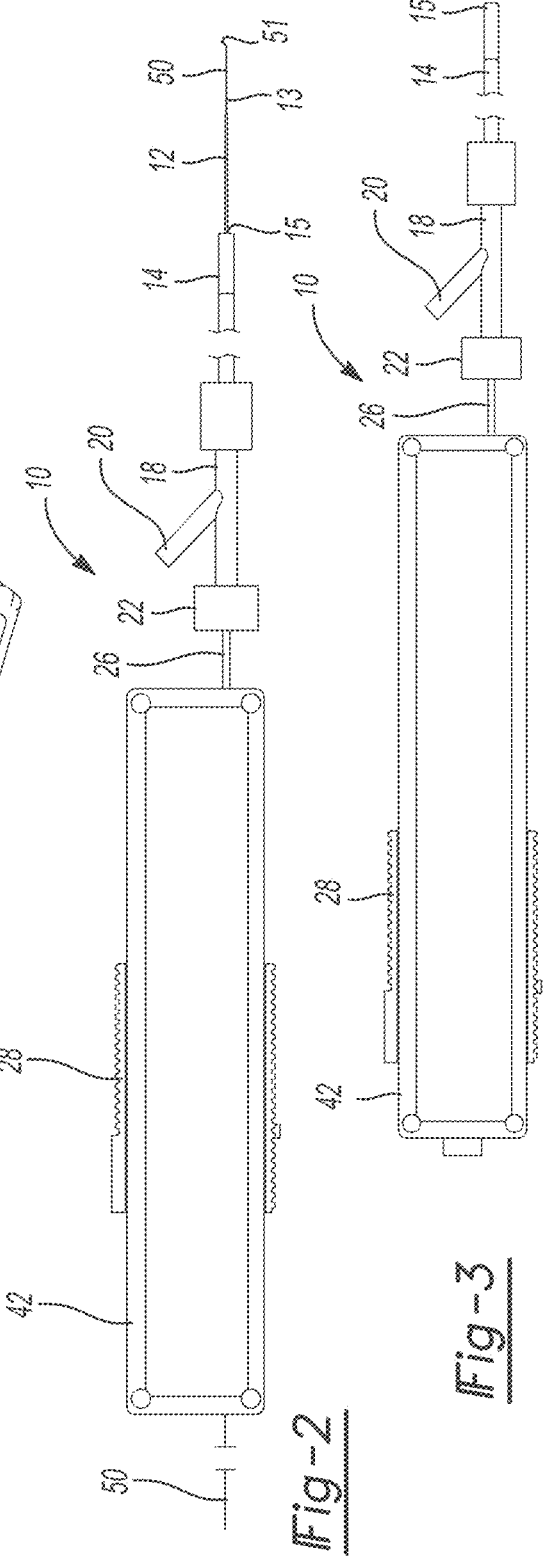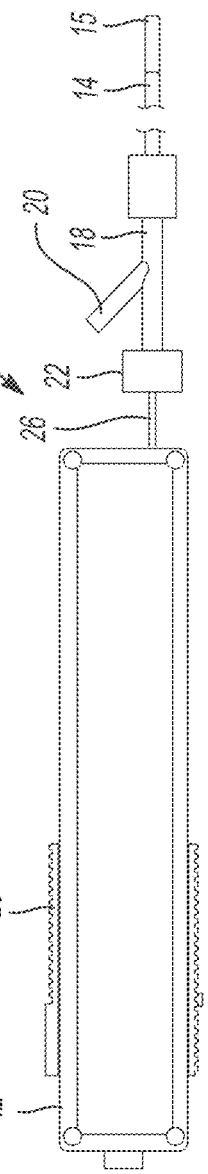

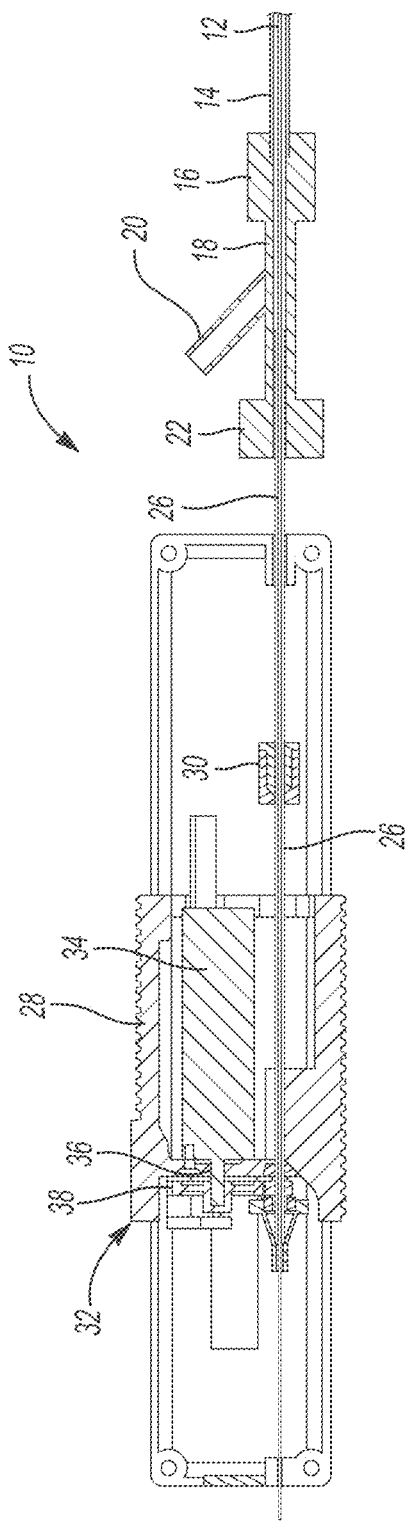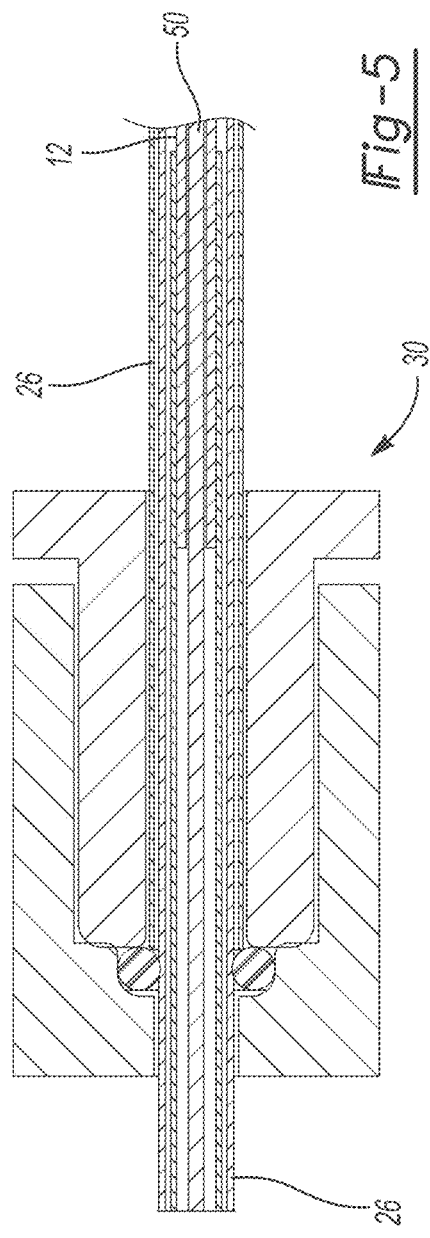

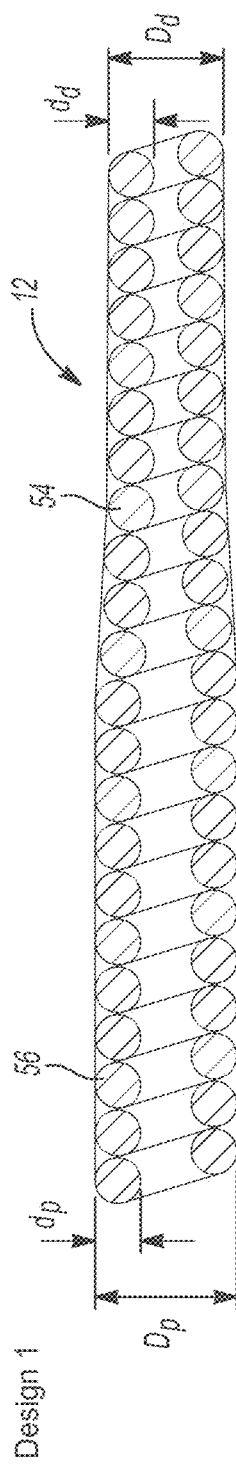
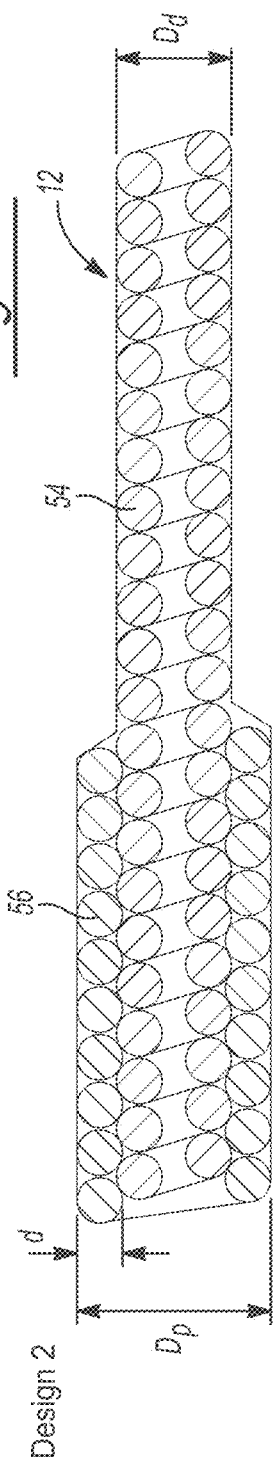
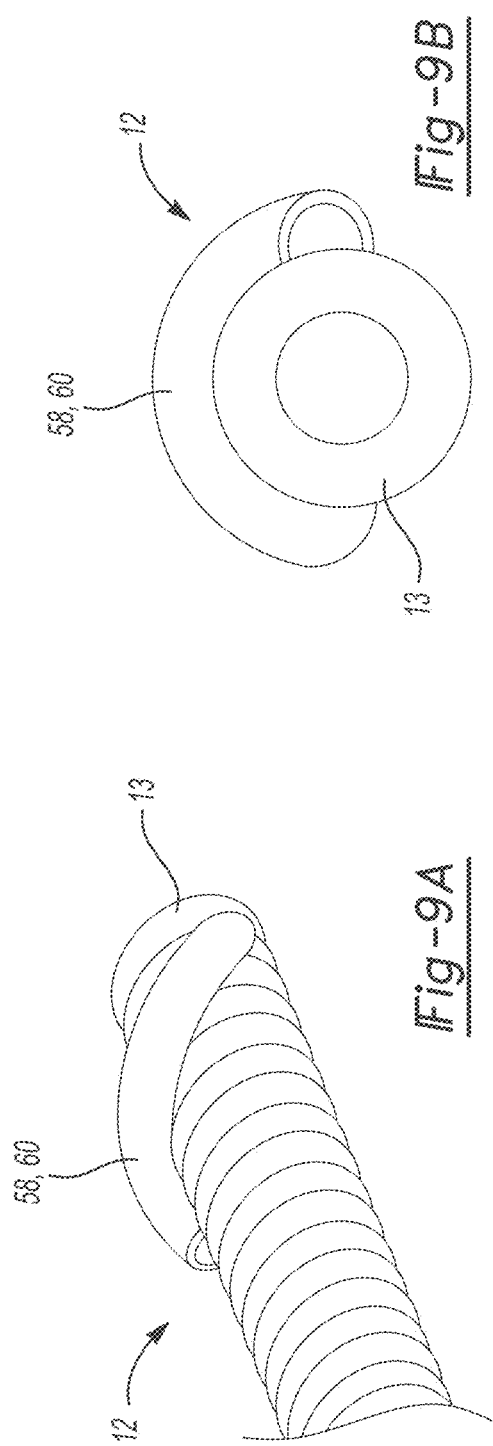

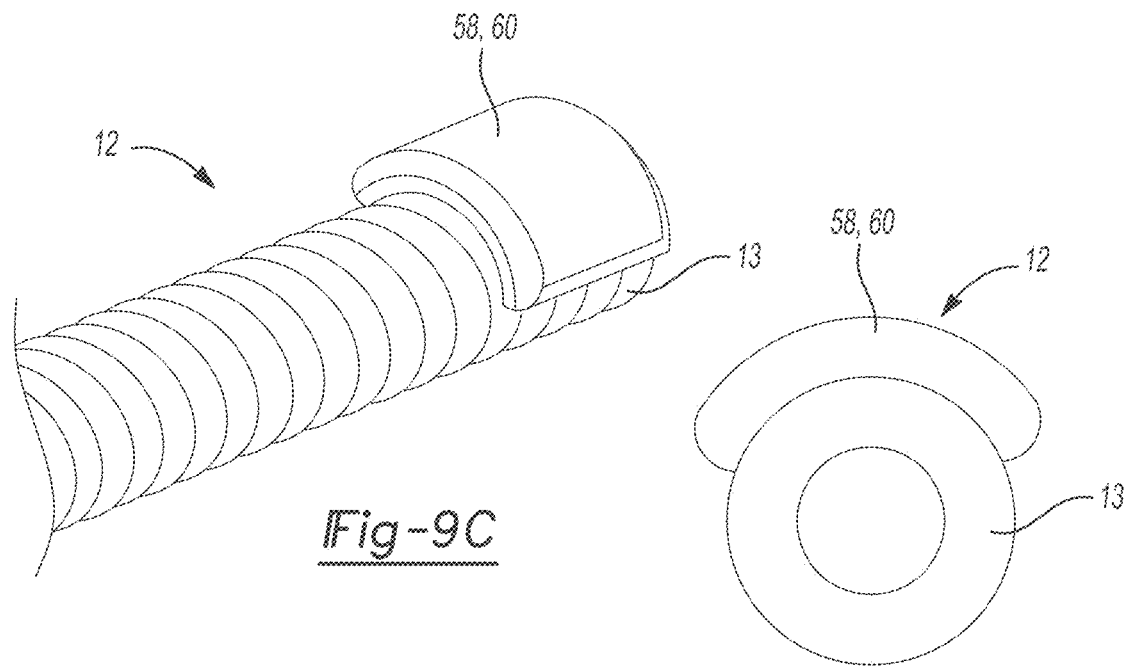
Fig-9C
Fig-9D
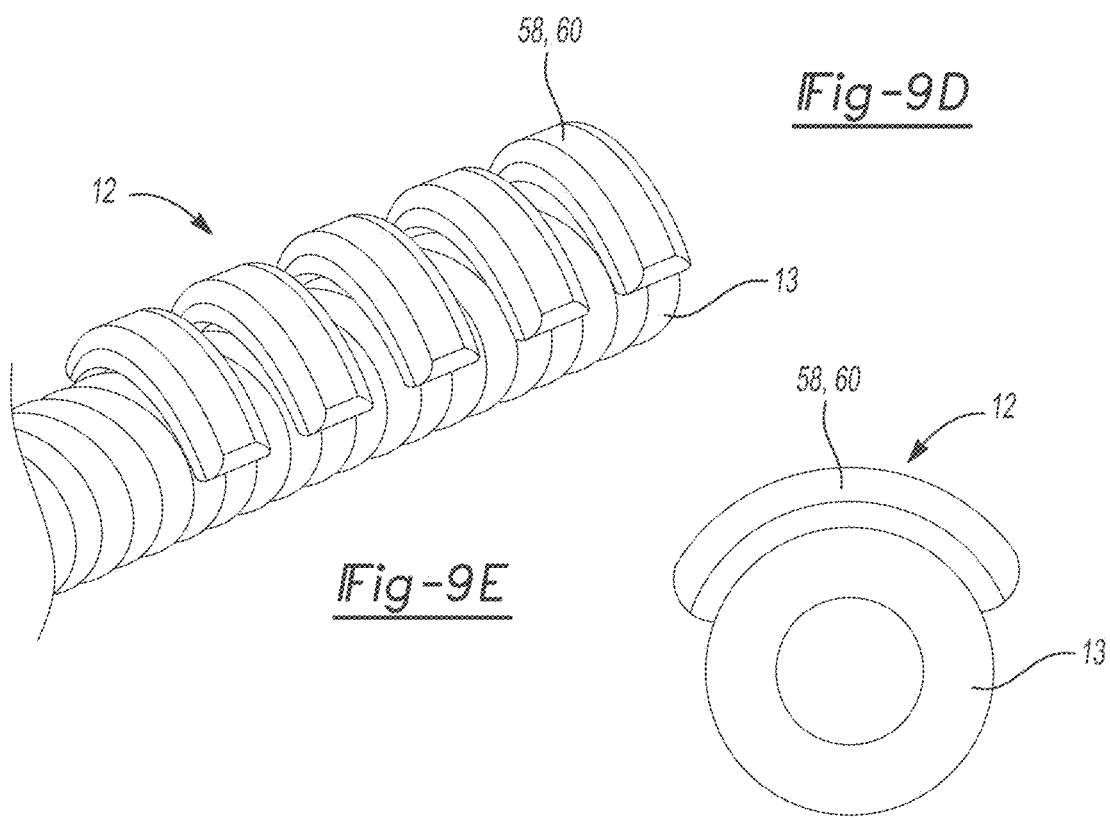
Fig-9E
Fig-9F

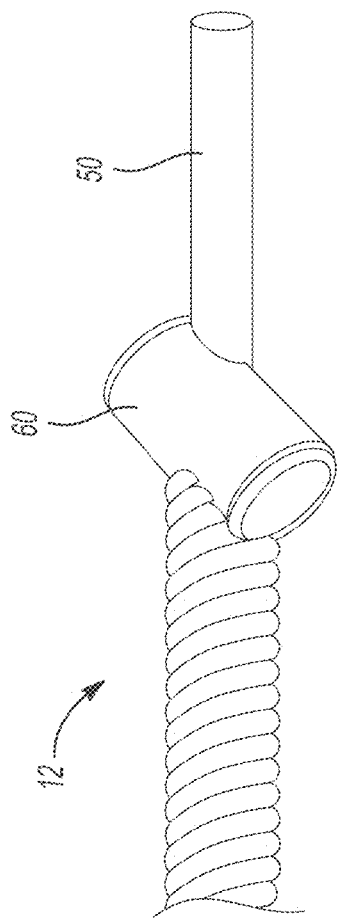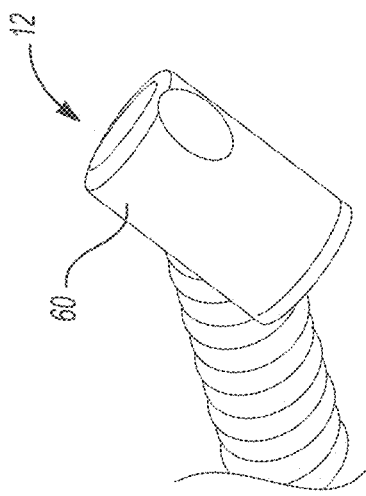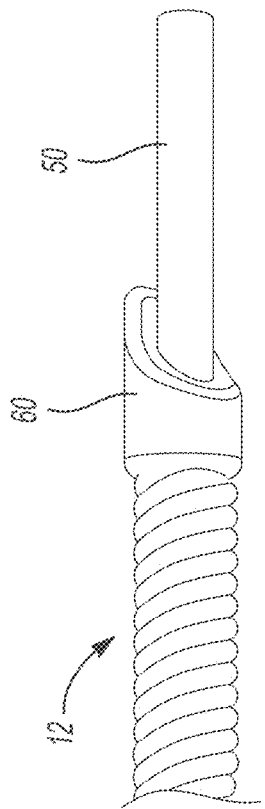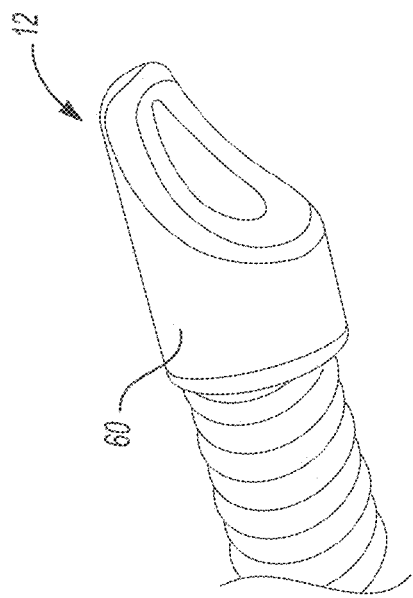
*Fig-10A*  *Fig-10B*  *Fig-10C*  *Fig-10D*

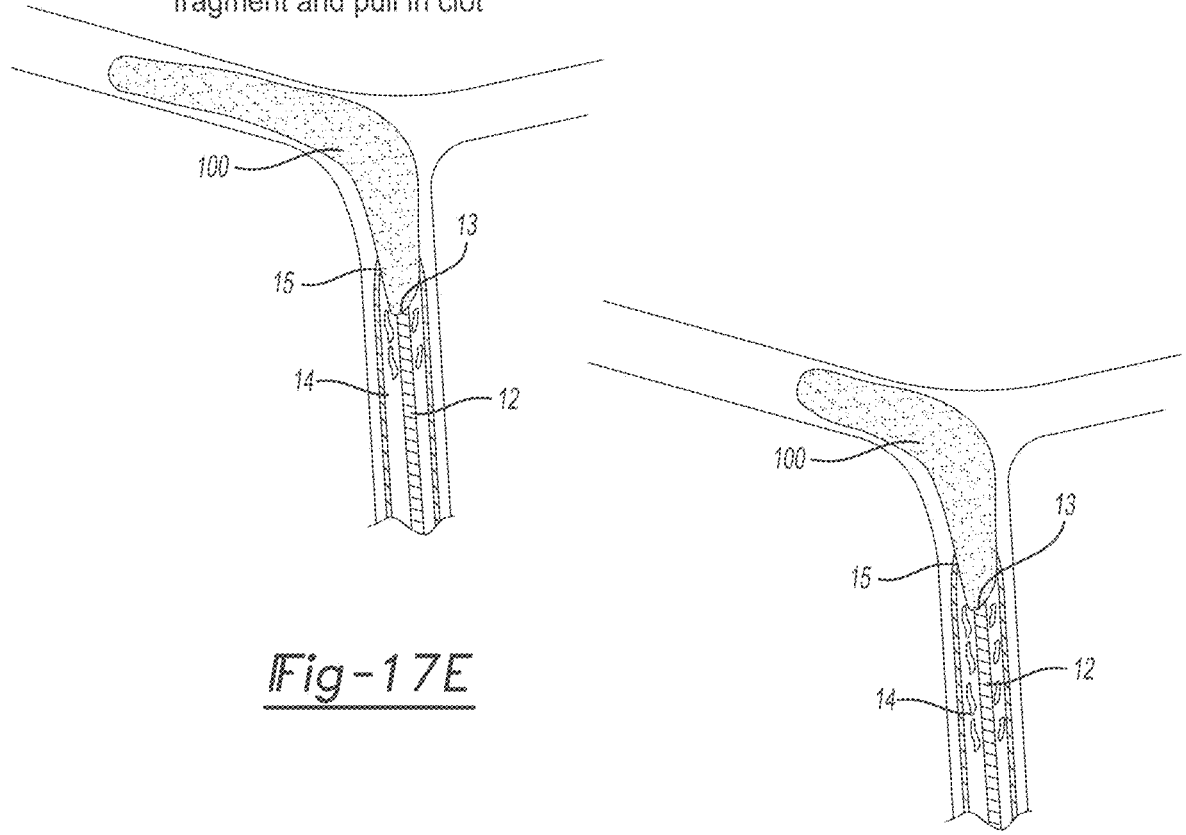
Fig-17E
Fig-17F
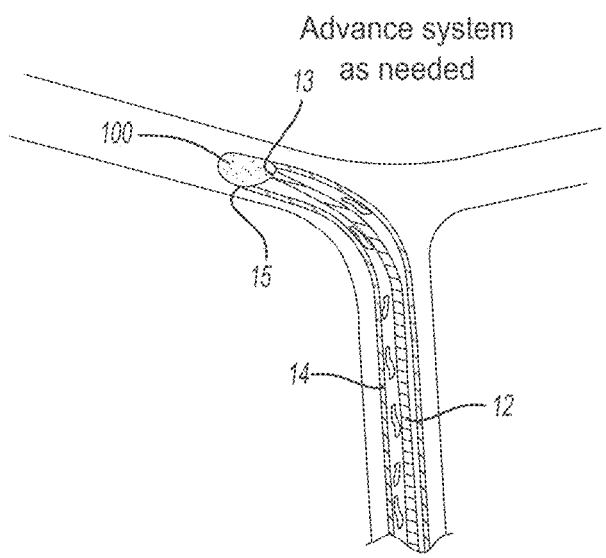
Fig-17G

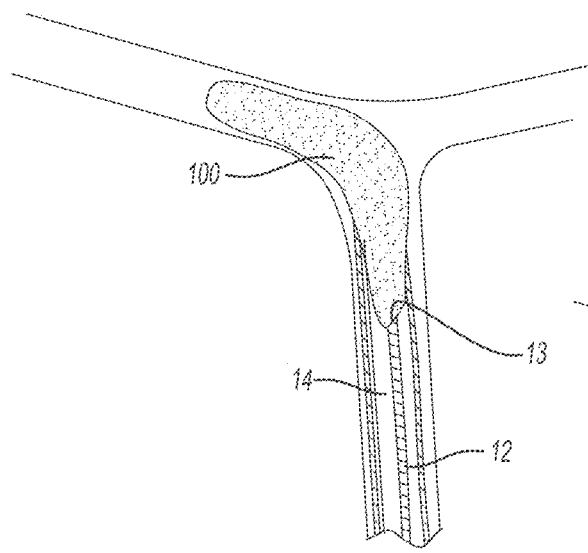
*Fig-18A*
In an alternative embodiment, tha gudewire can be located on the outside of the shaft, prefreable within the cathater wall to help navogation during the thrombeclomy
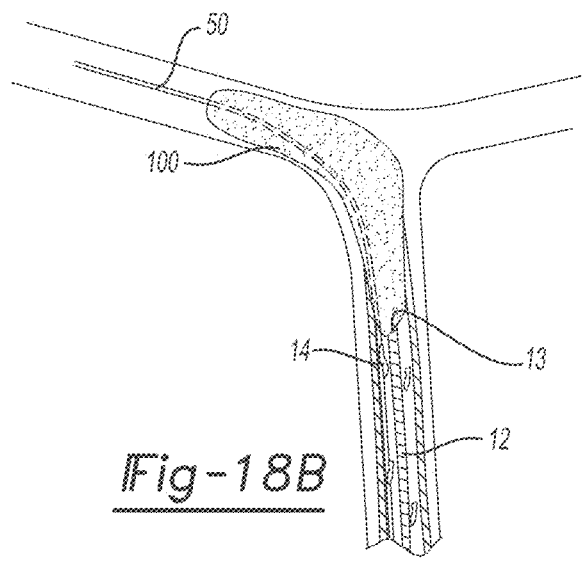
*Fig-18B*
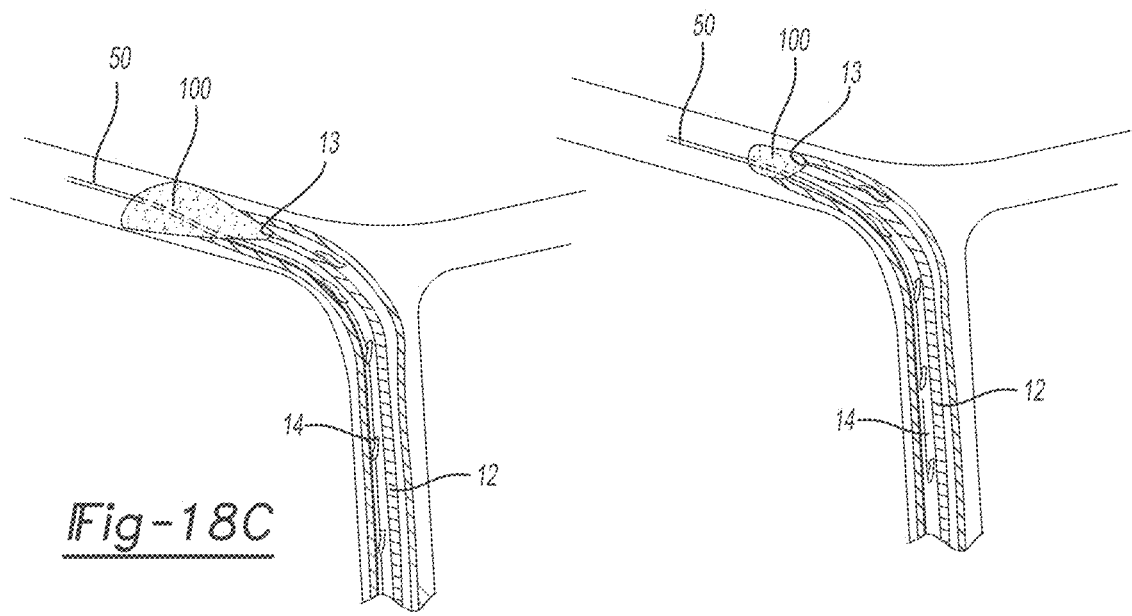
*Fig-18C*
*Fig-18D*

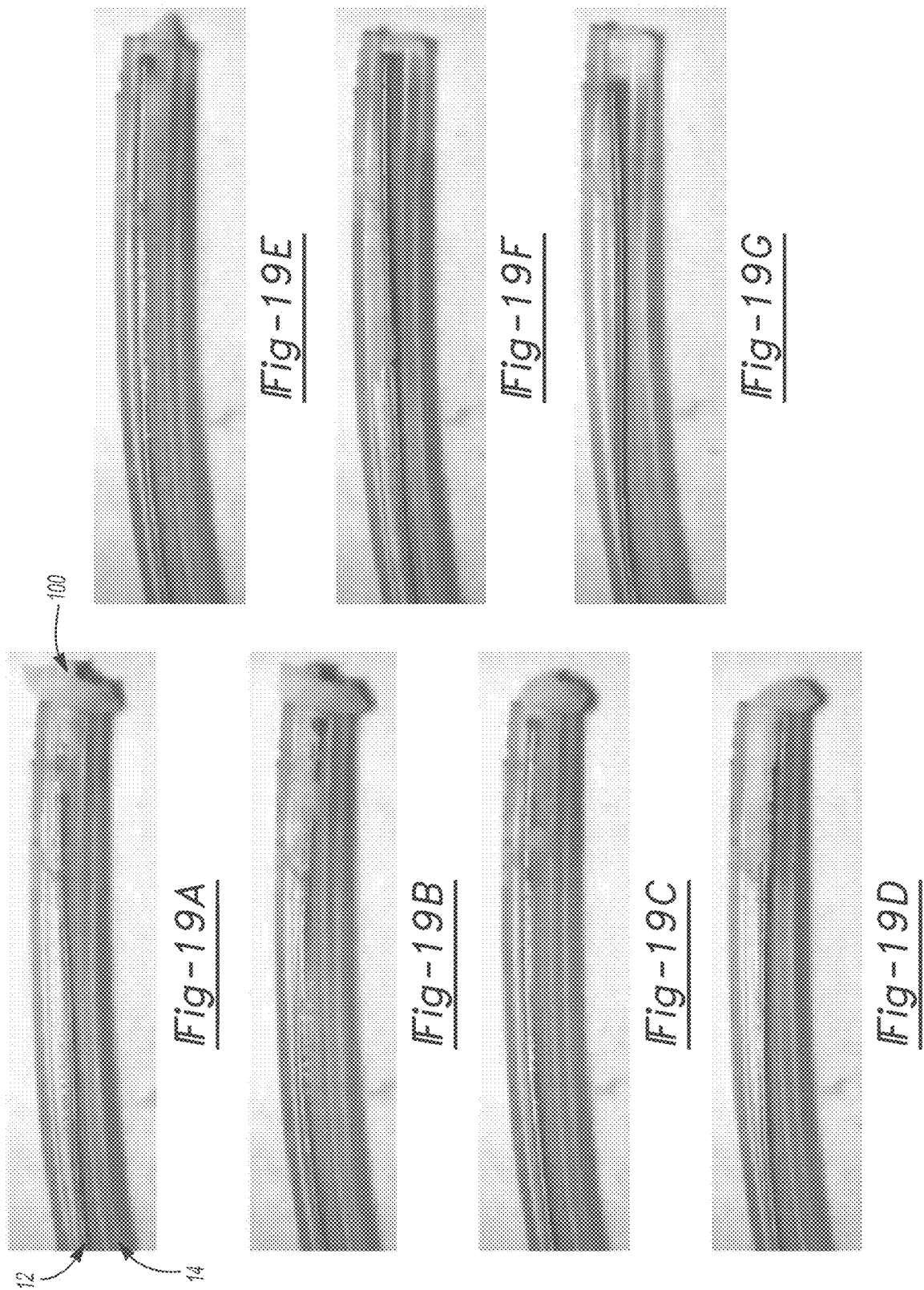

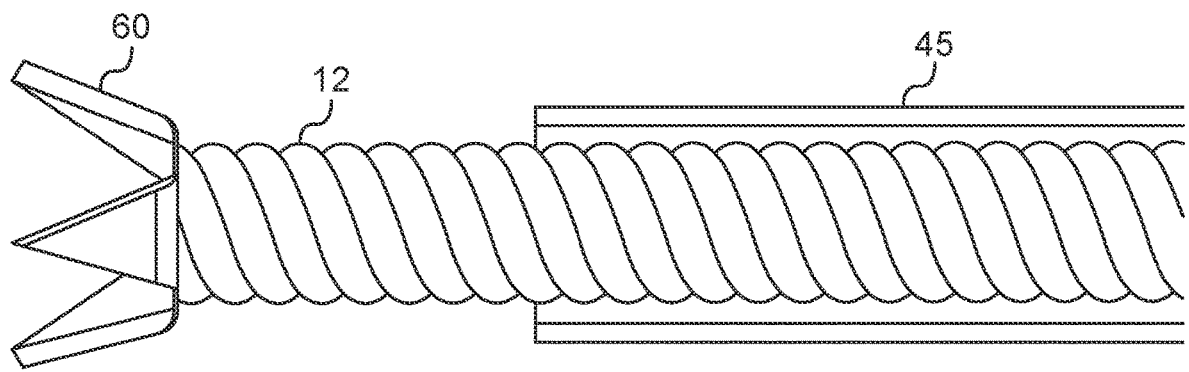
FIG. 25B
FIG. 26A
FIG. 26B
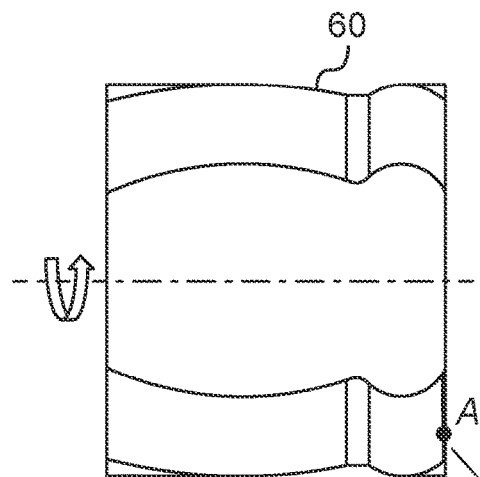
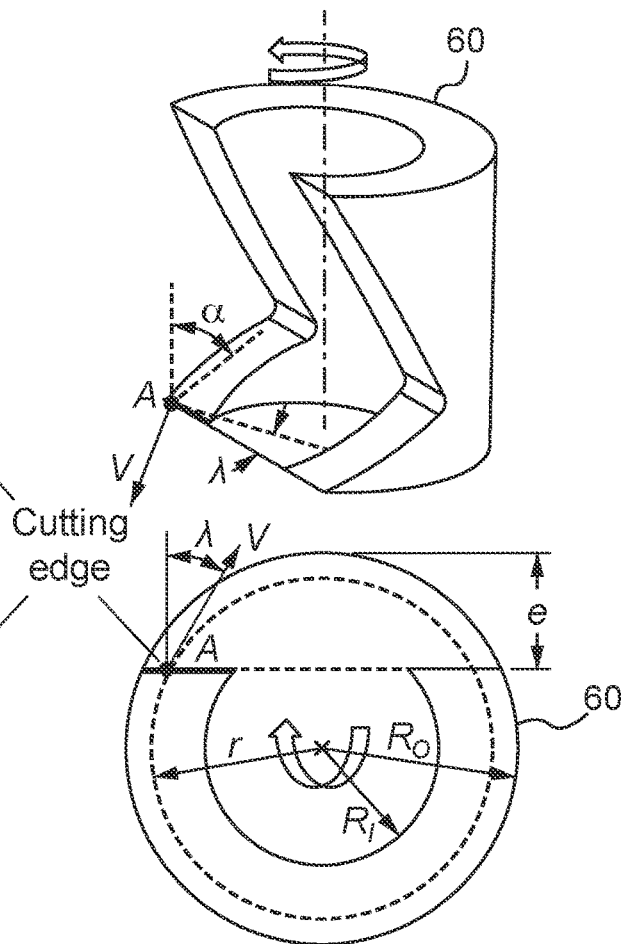
Cutting edge
FIG. 26C
FIG. 26D

HYDRODYNAMIC VORTEX ASPIRATION CATHETER

CROSS-REFERENCE TO RELATED APPLICATIONS

This application is a continuation of PCT International Application No. PCT/US2019/026737, filed on Apr. 10, 2019, which is a continuation-in-part application of U.S. patent application Ser. No. 16/156,519, filed Oct. 10, 2018, which is a continuation-in-part of PCT International Application No. PCT/US2018/026831, filed on Apr. 10, 2018, which claims the benefit of U.S. Provisional Application No. 62/483,580, filed on Apr. 10, 2017. This application is also a continuation-in-part of U.S. patent application Ser. No. 16/156,519, filed Oct. 10, 2018. The entire disclosures of each of the above applications are incorporated herein by reference.

FIELD

The present disclosure relates to catheters and, more particularly, relates to an aspiration catheter augmented by hydrodynamic vortices that are generated by high-speed rotation of a flexible shaft.

BACKGROUND AND SUMMARY

This section provides background information related to the present disclosure, which is not necessarily prior art. This section provides a general summary of the disclosure, and is not a comprehensive disclosure of its full scope or all of its features.

Thrombosis is the formation of a blood clot inside a blood vessel, obstructing the flow of blood through the circulatory system. The formation of a thrombus can occur within the heart or any artery or vein in the body, leading to a myriad of medical problems such as myocardial infarction, stroke, pulmonary embolism, and deep venous thrombosis. Rapid thrombectomy is frequently needed in cases of 1) obstruction of arteries of delicate organs, such as the heart or the brain; 2) large clots interrupting blood flow in major vessels or causing severe symptoms; or 3) when systemic delivery of the drugs is too risky.

Multiple thrombectomy devices have emerged in the last decades. However, these devices continue to be largely ineffective with large clot burden, "organized" (i.e. thick) clots, and clots extending from large to small vessels, and many such devices cause distal embolization of clots and vascular damage as they dispose the cutting or macerating mechanism directly into the vascular lumen. In addition, devices are generally specific for a certain lumen size, which translates to the need of combining multiple sizes and types of devices in the same procedure. Mechanical thrombectomy in stroke presents additional challenges based on the tortuosity of vessel and the delicate nature of vessel walls. In this regard, mechanical thrombectomy mechanisms that have been successfully used in the peripheral vasculature to remove clots, some of which are described below, are too bulky and stiff for navigating the complex cerebral artery geometries, release many clot particles downstream leading to microvascular occlusion, or are too abrasive for delicate brain arterial walls.

Modification of catheter shape has been suggested or disclosed in the prior art to enhance aspiration of intravascular clots. In U.S. Pat. No. 8,075,510 to Aklog et al., a suction cannula is described with a distal end that is deployable to expand from a first diameter to a relatively larger second diameter with a funnel shape. The differential diameter is believed to induce a laminar flow circumferentially along the interior surface of the funnel to generate a vortex flow into the distal end of suction cannula. In the presence of a vortex flow, such a flow can act to direct the undesirable material toward the distal end to allow the material to subsequently be pulled into the distal end by suctioning.

Other systems and methods have been disclosed in the prior art to achieve thrombectomy based on waterjet thrombectomy catheters. The catheters described may have proximal-to-distal waterjet flow, such as U.S. Pat. No. 5,135,482 to Neracher, or distal-to-proximal-directed waterjet flow past a window, orifice or gap at the distal end of the catheter, re-entering the catheter and pushing flow through an evacuation lumen, such as in U.S. Pat. No. 6,676,637 to Bonnette et al. The Bonnette Patent describes a dual catheter assembly with the inner tube having a high-pressure lumen with a distally located jet emanator having one or more rearwardly directed orifices for directing one or more jets of saline toward the distal end of a flow director which fragments and drags clots into the outer larger catheter.

Catheter-based instruments with different macerating mechanisms have been suggested or disclosed in the prior art for to fragment clots for thrombectomy in the vascular lumen with revascularization of arteries and veins. With these devices, the clot is broken into smaller pieces, most of which migrate further downstream, decreasing the central obstruction. U.S. Pat. No. 5,876,414 to Straub discloses a catheter for clearing a vessel composed by a rotary drive mechanism that rotates a helical shaped cutting tool. As the rotor rotates, dual cutting slots engage and sever the material along the vessel wall. U.S. Pat. No. 6,238,405 to Findlay discloses another catheter device for removing material having a rotatable screw thread distal end adjacent a shearing member also near the distal end. By application of the "Archimedes" screw action, in combination with vacuum, thrombus is drawn into the device in order to be macerated by shear and removed. U.S. Pat. No. 5,695,507 to Auth describes a helically wound coil wire delivered through a catheter with or without vacuum that is disposed outside the catheter within the clot mass in the arterial lumen and rotated at a preferable speed of 500 to 6000 rpm to cause fibrin to be wound around the shaft. As the fibrin fibers follow the rotating core, they are eventually stripped away from the clot, which loses its structural network. This leads to release of red blood cells back into the circulatory system, since the insoluble material is retained on the core wire for later extraction from the body. U.S. Pat. No. 6,090,118 discloses a mechanical thrombectomy device with a wire that extends distal to a catheter and is rotated to create a standing wave to break-up or macerate thrombus. U.S. Patent Publication No. 2002/0173812 discloses a thrombectomy wire that has a sinuous shape at its distal end and is contained within a sheath in a substantially straight non-deployed position. When the sheath is retracted, the distal portion of the wire is exposed to enable the wire to return to its non-linear sinuous configuration. Actuation of the motor causes rotational movement of the wire, creating a wave pattern, to macerate thrombus. Other sinuous or s-shaped rotatory wires to disrupt clots are disclosed in U.S. Pat. Nos. 9,282, 992 and 6,926,725, and U.S. Patent Application Publication Nos. 2004/0006306, 2017/0007290, and 2017/0007290. The abovementioned devices are not intended to pass through tortuous pathways found in the fragile brain vessels as they would release clot material downstream leading to strokes, or the actuation of the macerating mechanism disposed directly in the vascular lumen would lead to vascular damage of delicate vessels.

Another rotary thrombectomy mechanism is disclosed in US 2016/0166266 by Nita with a rotating longitudinal element with a shaped tip disposed within an aspiration catheter. This rotating element is advanced to position after the aspiration catheter has reached the target with the help of ancillary "support elements", such as intermediate catheters. In order to advance the rotating element to position near the end of the catheter through complex anatomy, it must have sufficient stiffness to be pushed without kinking or looping. In addition, the rotational element is constructed with sufficient stiffness to serve as a clot macerating tool. The required stiffness of the rotatory elements in this prior art, along with the inability to be co-axially navigated over an inner guidewire, would preclude its use for atraumatic navigation within the vasculature beyond the tip of the aspiration catheter. To completely prevent the distal tip of the rotational member from being exposed outside the aspiration catheter, the rotating element includes a stopper by design. Additionally, the required stiffness of the rotary element creates large radial forces against the inner wall of the catheter, leading to high friction and rapid wear of the catheter. This is especially relevant if the rotating element acquires corkscrew motion upon high speed rotation, requiring the mechanism to operate below torque load needed to generate hydrodynamic vortices. The prior art does not disclose a stand-alone device suitable for both navigation into narrow and highly tortuous vasculature and the ability to clear occlusive material by rotatory-induced hydrodynamic vortices. Such a technology would be challenging to develop as the features needed for safe intravascular navigation are generally contraposed to the features needed for efficient clot removal.

The present teachings overcome the shortcomings of the prior art to create a device for both atraumatic navigation into tortuous vasculature and mechanical thrombectomy. According to the present teachings, the same components that enable safe and efficient intravascular navigation provide clot removal, leading to highly efficient and effective interventions. This multimodal thrombectomy device design for navigation and thrombectomy is achieved by the invention of an actuated telescoping system that allows coaxial and steerable advancement of the device to target, and the generation of forces leading to rapid and effective thrombectomy. The device contains a flexible navigation system that can be atraumatically deployed within complex vasculature with or without a guidewire. This navigation system provides "scaffolding" (by itself, or based on the coupled stiffness of the guidewire inside the navigation element's lumen and the navigation element itself, or by the coupled stiffness of additional intermediate catheter(s) that also telescope to create a coupled system) to enable the coaxial advancement of one or more larger diameter aspiration catheters to challenging targets. These navigation elements can subsequently be shielded within a catheter and actuated as a thrombectomy system in cooperation with external vacuum to generate hydrodynamic vortices and corkscrew movements for clot removal. In some embodiments, the telescoping system composed by guidewire, a navigation/thrombectomy rotational element (henceforth named "shaft") and a catheter collectively constitute a tri-axial system. This system is well suited to navigate highly tortuous, but delicate, anatomy, but at the same time provide the needed scaffolding to allow the advancement of big bore suction catheters, as it is frequently needed to remove clot in large vessel occlusion in stroke.

In some embodiments, the telescope system can also be constructed by a tapered and steerable shaft that can be disposed within the vascular lumen without the co-axial use of a guidewire. In this embodiment, the shaft can be guided and advanced into the vascularity and provide scaffolding for catheter advancement to target during navigation mode. Upon proximity with the occluding material, the shaft can be actuated facilitating clot removal. This bi-axial telescoping system can enable significant downscaling to reach smaller vessels, such as distal cerebral arteries, while maintaining maximum vacuum and enabling the generation of thrombectomy forces upon high speed rotation of the steerable shaft.

In some embodiments, the tri-axial telescoping system can be complemented by the addition of one (i.e. tetra-axial system) or more telescoping catheters for enhanced navigation and thrombectomy. The additional telescoping catheter (henceforth named "sleeve") can be disposed co-axially between the shaft and the suction catheter and be designed to have uncoupled movements with the other components of the telescoping system. During navigation mode, the sleeve can be disposed at least partially over the shaft to minimize kinking and looping of the flexible shaft upon forward advancement into the vasculature. The sleeve can also enhance the scaffolding function of the shaft while decreasing the shelf (gap between shaft and catheter) to advance a large bore suction catheter co-axially. In addition, during navigation mode the sleeve can be disposed over the shaft at least partially to shield thrombectomy enhancing features of the shaft that would be unsafe to be directly exposed to the vascular surfaces, or to provide enough stiffness to the advancing shaft and guidewire to penetrate the obstructing clot mass and allow the catheter to enter the clot mass rather than be pushed back or aside between the clot and the artery. During thrombectomy, the sleeve can be retracted to unsheathe thrombectomy enhancing features of the shaft, unleash the highly flexible shaft to generate thrombectomy forces upon high speed rotation, and increase the available cross-sectional lumen to facilitate clot engaging and removal with maximal vacuum power. The sleeve can be also advanced over the shaft to unload the shaft of clot debris. In addition, the sleeve can provide a channel to deliver solutions to the catheter tip before, during and/or after the procedure. None of these elements need to be completely removed from the system in order for the system to operate correctly, allowing rapid transitioning between navigation/thrombectomy modality and function.

In some embodiments, the shaft can be shorter than the telescoping system and disposed distally within the aspiration catheter. The shaft can be connected to one or more wires controlled by the actuator module that are extending inside, outside or within the wall of the aspiration catheter. The wire can be advanced towards the catheter, which causes the shaft to emerge from the catheter and advance into the vascular lumen as a navigation element (this can be supported by the use of a co-axial guidewire if needed inside the shaft). In this position, the shaft provides scaffolding for catheter advancement to target during navigation mode. After advancing the catheter to target, the shaft can be retracted into the catheter lumen by withdrawing the wire and can be actuated to generate vortices forces for thrombectomy. The actuation of the shaft can be driven by rotation of the wire through a system of gears and belts or alike or through injection of pressurized solution into a water wheel or alike. The wire adjusting the position of the shaft can be a monofilament, coil or braid. The telescope system in this embodiment maximize vacuum efficiency and flow by reducing the extend of shaft disposed within the suction catheter, and optimized torque transmission while reducing wear and tear by disposing a wire, rather than a shaft, in the segments of the telescope system traversing tortuous anatomy.

According to the teachings of the present invention, this technology provides an integrated mechanism for enhanced navigation into the target vessel and complete recanalization by anchoring and removing the obstructive thrombus by innovative thrombectomy mechanisms here disclosed. Such a system capable of reversibly transitioning between navigation and thrombectomy modes by differentially disposing and actuating multiple telescoping components would enable faster, more efficient and simpler removal of thromboembolic material.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is an exploded perspective view illustrating an aspiration catheter system according to the principles of the present teachings.

FIG. 2 is a side view of the aspiration catheter system according to the principles of the present teachings with the guidewire installed and the navigation element extended beyond the distal tip of the aspiration catheter.

FIG. 3 is a side view of the aspiration catheter system according to the principles of the present teachings with the guidewire removed and the navigation element retracted at the distal opening or within the aspiration catheter.

FIG. 4 is a cross-sectional view illustrating the aspiration catheter system according to the principles of the present teachings.

FIG. 5 is a cross-sectional view illustrating the telescoping hypotube seal according to the principles of the present teachings.

FIGS. 8C-8D are schematic cross-sectional views illustrating varying profiles of the flexible shaft.

FIGS. 9A-9F are perspective views and end views of a flexible shaft having hydraulic inducing features and/or eccentric features according to some embodiments of the present teachings.

FIGS. 10A-10D are perspective views and end views of a flexible shaft having eccentric features according to some embodiments of the present teachings.

FIGS. 17A-17G are schematic views illustrating the method according to some embodiments of the present teachings.

FIGS. 18A-18D are schematic views illustrating the method according to some embodiments of the present teachings.

FIGS. 19A-19G are partial cross-sectional views of the catheter and flexible shaft illustrating the corkscrew or helical motion of the flexible shaft during thrombectomy according to some embodiments of the present teachings.

FIG. 25B is a side view illustrating an unsheathed deployable element disposed on the flexible shaft and extending from the sleeve.

FIGS. 26A-26D are perspective views and end views of a shaft tip for use with the flexible shaft according to some embodiments of the present teachings.

Corresponding reference numerals indicate corresponding parts throughout the several views of the drawings.

DETAILED DESCRIPTION

Figure 6:
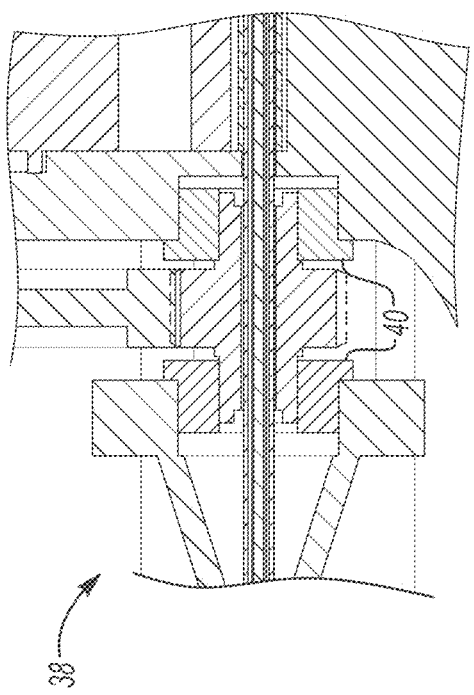
FIG. 6 is a cross-sectional view illustrating the gear set according to the principles of the present teachings.

Example embodiments will now be described more fully with reference to the accompanying drawings. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer, or section discussed below can be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Figure 16A:
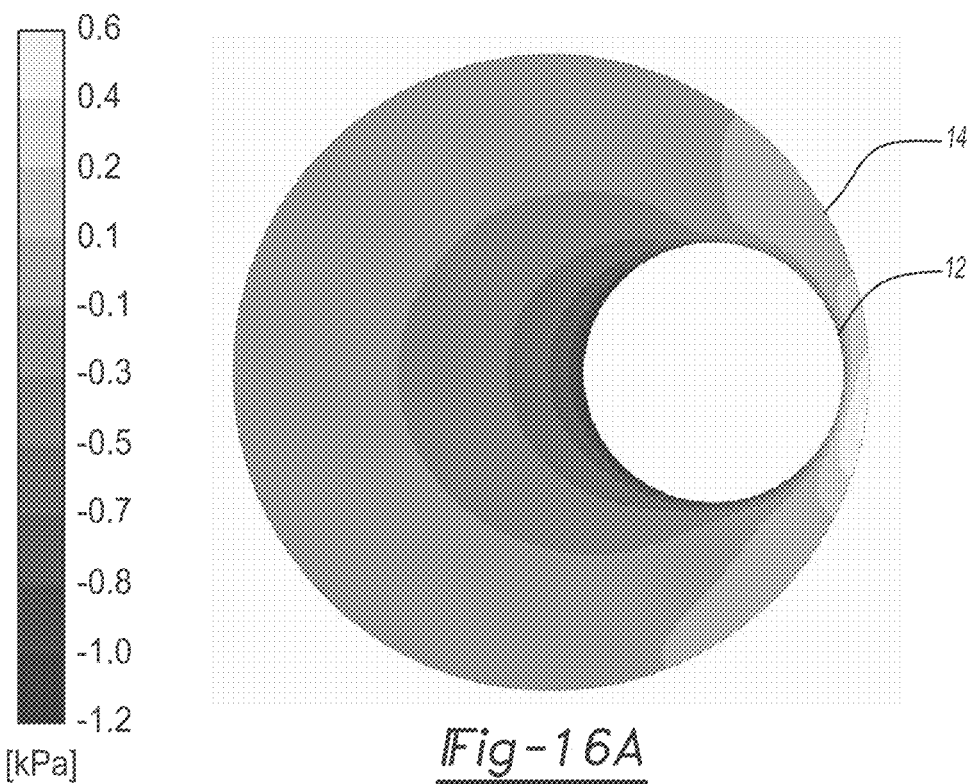
FIG. 16A is a graph illustrating the orbital translation of the flexible shaft within the catheter during thrombectomy.

According to the principles of the present teachings, an aspiration catheter system 10 implementing hydrodynamic vortices generated by rotation of a flexible shaft 12 is provided having an advantageous construction and method of use that is particularly configured to generate hydraulic forces and translational movements to engage, pull-in, fragment, and/or remove clot 100 or other obstructing material (collectively referred to herein as "clot 100") in cavities, organs or lumens. As will be described in detail herein, flexible shaft 12 rotates at a high speed with uncoupled rotation of the shaft and translational motion within at least an area defined by the internal wall of catheter 14 within which it is disposed. Generally, flexible shaft 12 rotates at speeds greater than 10,000 RPM during thrombectomy mode. FIG. 16A illustrates the pressure field on a cross section of the catheter with flexible shaft 12 rotating at 90,000 RPM from the computational fluid dynamics modelling. The rotating flexible shaft 12 drives the fluid surrounding it to rotate in the same direction and creates a pressure gradient across the gap between shaft 12 and catheter wall 17. This pressure gradient pushes flexible shaft 12 to do orbital translation inside catheter 14. This orbital translational motion, together with the hydrodynamic force and phase lag of mass elements along the length of the shaft 12, induces vortex capable of causing the flexible shaft 12 to actuate in corkscrew fashion at least partially within the catheter 14. In some embodiments, the rotation of flexible shaft 12 is not directly correlated with the translational motion of flexible shaft 12 inside catheter 14. This translational motion of the rotating flexible shaft 12 can be normal, parallel, or any combination thereof with respect to a plane which is normal to the center axis of containment catheter 14. In some embodiments, aspiration catheter system 10 comprises a vacuum source fluidly coupled to catheter 14.

With particular reference to FIG. 1, in some embodiments, aspiration catheter system 10 comprises flexible shaft 12 disposed within catheter 14. Catheter 14 can be selectively coupled to a catheter connection point 16. Catheter connection point 16 enables catheter 14 to be selectively removed, replaced, detached, or otherwise manipulated relative to the remaining portions of aspiration catheter system 10. In some embodiments, catheter connection point 16 permits independent rotation of catheter 14 with regard to the rest of aspiration catheter system 10 to improve navigation ability.

Catheter connection point 16 can be attached or integrally formed with a vacuum port assembly 18 having a vacuum port 20 and an adjustable catheter sliding lock 22. Vacuum port 20 is operably coupled to a vacuum source 24 for exerting a vacuum pressure within catheter 14 and at a distal end 15 of catheter 14 to suck clot 100 into distal end 15 of catheter 14 and into vacuum port 20 in accordance with the principles of the present teachings. Vacuum port 20 can be "Y" shaped, "L" shaped, "T" shaped or "tri-Y" shaped. In some embodiments, the vacuum pressure is delivered in dynamic fashion by changing pressures at different frequencies between approximately 0.5 Hz and 1000 Hz with magnitude between approximately −100 kPa to −5 kPa on a gauge pressure scale. In some embodiments, the vacuum pressure is constant.

In some embodiments, catheter sliding lock 22 enables customizable spacing of flexible shaft 12 and the distal end 15 of catheter 14. In some embodiments, catheter sliding lock 22 can be adjusted such that a distal end 13 of flexible shaft 12 is within a maximal clot busting zone without protruding beyond it. In some embodiments, distal end 13 of flexible shaft 12 does not extend beyond distal end 15 of catheter 14. This is particularly useful in applications where contact of flexible shaft 12 and the associated tissue is to be avoided. In some embodiments, distal end 13 of flexible shaft 12 extends beyond distal end 15 of catheter 14. This is particularly useful in applications where contact of flexible shaft 12 and the associated tissue is desired.

In some embodiments, vacuum port assembly 18 is coupled to telescoping hypotubes 26 that permit a flexible shaft advancement slider 28 to move flexible shaft 12 along the longitudinal axis of catheter 14 to facilitate navigation of distal end 15 of catheter 14. In some embodiments, the flexible shaft advancement slider 28 enables the flexible shaft 12 to extend beyond the distal tip 15 of catheter 14 by a distance of greater than at least 10 mm, preferably at least 80 mm. Hypotubes 26 can extend along a telescoping hypotube seal 30 that allows the hypotubes 26 to telescope while maintaining a seal to help prevent vacuum loss (by preventing vacuum loss in all parts of the device besides distal end 15 of catheter 14), thereby maximizing the vacuum and thrombectomy power at distal end 15 of catheter 14. A hypotube clamp 31 secures telescoping hypotubes 26 to flexible shaft advancement slider 28 for facilitation by an operator. More particularly, flexible shaft advancement slider 28 enables the user to selectively advance flexible shaft 12 beyond distal end 15 of catheter 14, thereby helping to facilitate navigation in the vessels. FIG. 2 illustrates flexible shaft 12 and a guidewire 50 advanced beyond distal end 15 of catheter 14 for navigation. FIG. 3 illustrates guidewire 50 removed and flexible shaft 12 locked into position within catheter 14 for thrombectomy.

In some embodiments, aspiration catheter system 10 can comprise a momentary adjustment system 29 to fine tune or adjust distal end 13 of flexible shaft 12 relative to distal end 15 of catheter 14. In other words, adjustment system 29, as illustrated in FIGS. 20A-23A, can provide a variable adjustment system to adjust the relative spacing of distal end 13 of flexible shaft 12 to distal end 15 of catheter 14. Adjustment system 29 can be configured to permit fine tuning of the relative spacing and can be set to this relative spacing distance. However, adjustment system 29 can further be used for instantaneous and/or momentary adjustment of flexible shaft 12 relative to catheter 14. In some embodiments, adjustment system 29 can comprise a rotating screw member 33 threadedly coupled to shaft adjustment device 25 slidably disposed in housing 42. Shaft adjustment device 25 is releasably connectable with shaft adjustment slider 28 via a latching arm or other means. A head of screw member 33 can be captured within a cavity 35 formed in a housing 42. A spring member 37 can be disposed between the head of screw member 33 and housing 42 to bias the head of screw member 33 away from housing 42 a predetermined distance, but can provide momentary advancement of flexible shaft 12 when desired. That is, upon a user pressing the head of screw member 33 against the biasing force of spring member 37, screw member 33 and shaft advancement device 25, and thus coupled shaft advancement slider 28 and flexible shaft 12, can be momentarily advanced longitudinally a distance approximately equal to the distance the head of screw member 29 is spaced from housing 42. However, rotation of screw member 33 causes threaded engagement with shaft advancement device 25 and coupled shaft advancement slider 28 to advance or retracts advancement slider 28 and flexible shaft 12 to a desired location relative to catheter 14.

By pressing on the head of screw member 33, flexible shaft 12 can be momentarily advance distally (in preferred embodiments, by about 1 mm-10 mm) to help flexible shaft 12 better engage clot 100 that is being aspirated by aspiration catheter system 10. In this teaching, as clot 100 is pulled in, it can act to push flexible shaft 12 proximally, potentially changing the relative distance between distal tip 15 of catheter 14 and flexible shaft 12.

By rotating screw member 33, shaft adjustment device 25 moves proximally or distally. Since shaft advancement slider 28 and flexible shaft 12 slide locks into this part before activating thrombectomy, the relative distance of shaft advancement slider 28 can adjust the relative distance between tip 13 of flexible shaft 12 and tip 15 of catheter 14. This is helpful for any fine tuning of distance.

In some embodiments, as illustrated in FIGS. 20A-23A, an aspiration catheter adjustment device 39 can be used to selectively adjust the relative spacing between tip 15 of catheter 14 and tip 13 of flexible shaft 12. In this embodiment, aspiration catheter adjustment device 39 comprises a lead screw 41 attached between housing 42 and adjustable catheter sliding lock 22, which when screwed in or out cause catheter 14 to move proximal or distal. Alternatively, shaft advancement slider 28 can comprise a slider locking point that is adjusted using a continuous mechanism or a discrete mechanism, such a multiple snap ridges (shown), to adjust the relative distance between catheter 14 and shaft 12 when in thrombectomy mode. This can be utilized at any point during the operation, before, after, or during thrombectomy.

With reference to FIGS. 1, 4, and 6, a drive system 32 is provided for rotatably driving flexible shaft 12 (e.g. providing rotational energy) in accordance with the principles of the present teachings. In some embodiments, drive system 32 comprises a motor 34 having an output shaft 36 operably coupled to a gear set 38 operably coupled to flexible shaft 12. In some embodiments, for improved packaging and efficiency, motor 34 is disposed within an internal space of shaft advancement slider 28. Flexible shaft 12 and/or gear set 38 can be rotatably supported by one or more bearings 40.

The components of aspiration catheter system 10 can be contained within a handheld, or other appropriately sized, housing 42.

Figure 23:
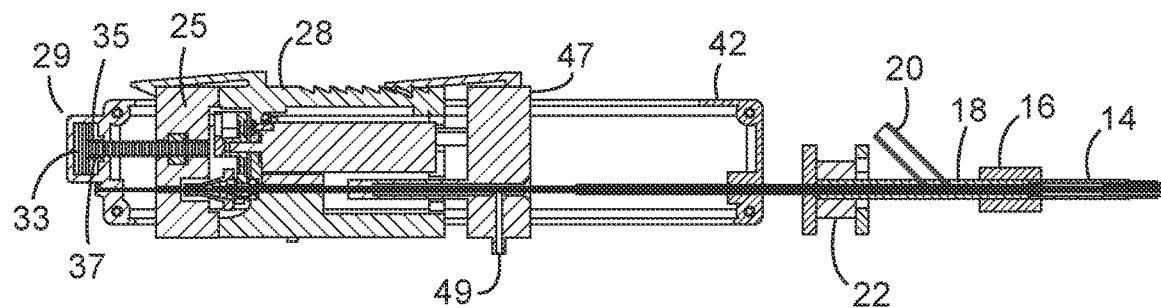
FIG. 23 is a cross-sectional view illustrating the aspiration catheter system of FIG. 20A according to the principles of the present teachings.
Figure 24:
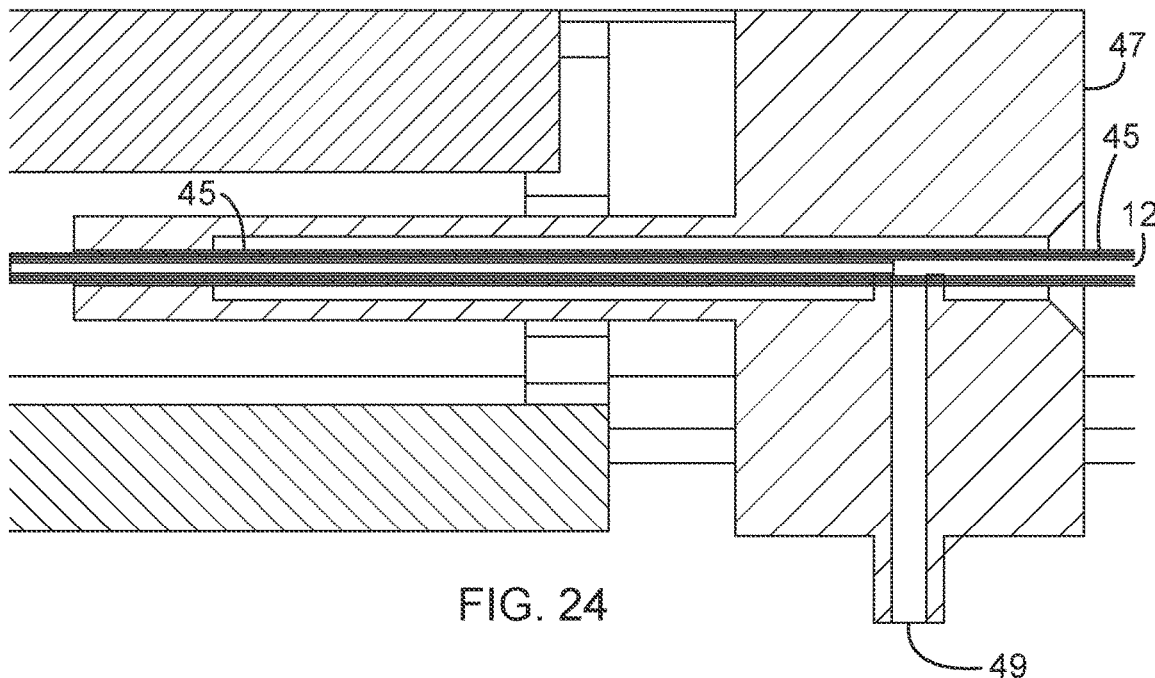
FIG. 24 is a partial enlarged cross-sectional view illustrating the aspiration catheter system of FIG. 20A illustrating a fluid port.

In some embodiments, as illustrated in FIGS. 23-24, one or more fluid ports 49 can be used to inject fluid into the lumen of a sleeve, flexible shaft 12, catheter 14, or a combination thereof. This can be useful to deliver medication, lubricating fluid, cooling agents, and fluid to help prevent cavitation during thrombectomy and maintain stable vacuum power and remove clots.

In some embodiment, the wire is introduced into the shaft via a "Y" valve featuring a rotational hemostatic valve and an infusion port to deliver saline solution, contrast agent or other solutions into the shaft lumen as needed.

In some embodiment, the actuation of the elements of the telescoping system can be controlled and actuated by a robotic platform. FLEXIBLE SHAFT With particular discussion relating to flexible shaft 12, it should be understood that in some embodiments flexible shaft 12 has sufficient flexibility to permit it to be bent or curved around tight corners (typically a radius of curvature smaller than 10 mm) and turn angles as large as 360 degrees without inducing permanent deformation for at least 1" most distal part of flexible shaft 12. In some embodiments, flexible shaft 12 is torque resistant such that flexible shaft 12 can transmit high rotational energy from drive system 32 to clot 100 without failure.

To this end, as illustrated in FIGS. 7A-7D, flexible shaft 12 can be solid, hollow, or a combination thereof, and/or braided or single stranded, or a combination thereof. Hollow and/or braided configurations can increase flexibility and torque resistance while assuring high transmission efficiency of rotational energy. In configurations employing a hollow flexible shaft 12 (see FIGS. 7B-7D), guidewire 50 can extend within hollow flexible shaft 12 (see FIG. 7C) to facilitate navigation of distal end 13 of flexible shaft 12 and/or catheter 14 through the vasculature and/or can extend within a hollow portion 52 of catheter 14 formed in a sidewall thereof (see FIG. 7D). In some embodiments, guidewire 50 can include a defined shape at its distal end 51, such as a J, U, or other shapes, if desired, to facilitate intravascular navigation. Guidewire 50 can optionally be steerable and be advanced outside flexible shaft 12 and outside distal end 15 of catheter 14 to facilitate advancement of flexible shaft 12 and catheter 14 into clot 100 and into the target vessel. Furthermore, flexible shaft 12 can also be selectively advanced beyond distal end 15 of catheter 14 and along the guidewire, creating additional scaffolding to help facilitate the advancement of catheter 14 to the desired position. Upon advancement of catheter 14 in the desired position, flexible shaft 12 can be withdrawn toward distal tip 15 of catheter 14 and even completely inside catheter 14 and the guidewire 50 can be withdrawn into flexible shaft 12 or completely outside the device as needed. Then, flexible shaft 12 is rotated at high speed to perform thrombectomy as described herein.

In a preferred embodiment for mechanical thrombectomy in stroke due to large vessel occlusion, in a particular device and operation the same flexible shaft 12 is used as "navigation element", "scaffolding element" and "thrombectomy element." These functions can be reversibly transitioned among them. This can be achieved through using a flexible and hollow shaft 12 that can be linearly actuated by shaft advancement slider 28 and be coupled as needed with a co-axial guidewire 50, and actuated by a drive system 32 at different modalities and intensities. None of these elements need to be completely removed from the system in order for the system to operate correctly.

The flexible shaft 12 is preferably smooth and has a tapered distal end (distal portion is preferably smaller in diameter compared to the proximal end). This flexible shaft 12, when acting as a "navigation element", can be atrau- matically advanced over a guidewire beyond the distal catheter opening (preferably at least 80 mm) into complex and highly tortuous vasculature. The use of a coaxial inner guidewire 50 can improve the ability of the shaft 12 to advance inside the catheter without kinking or looping which could prevent it from reaching the distal tip of the catheter and could also damage the shaft 12. In a tetra-axial system, a sleeve 45 can be added to enhance shaft advancement. When flexible shaft 12 is acting as a "navigation element", it can be provided with oscillating, rotational, translational, or vibrational motion, generated by the drive system 32 and/or the operator's hand. This powered "navigation element" can aid in the placement of guidewire 50, flexible shaft 12, and/or catheter 14 by reducing the friction between these coaxial elements and themselves and the vasculature. This will facilitate the aspiration catheter system 10 to advance through tortuous geometry, advance through irregular lumens and or stenosed geometry and facilitate advancement of a larger catheter.

The shaft 12 can serve as a "scaffolding element" by enabling the coaxial over-the-shaft advancement of catheter 14 to challenging targets in a manner substantially equivalent to an intermediate catheter. Although the flexible shaft 12 may be too flexible in some embodiments to allow standalone over-the-shaft advancement of catheter 14, the combination of the shaft 12 with an inner guidewire 50 can provide sufficient structure and stiffness for over-the-shaft advancement of the catheter 14. The advancement of the catheter 14 over the shaft 12 can be facilitated by one or a combination of oscillating, rotational, translational, or vibrational motion of the shaft 12, the catheter 14 or a combination of both, powered by the drive system 32 or the hands of the operator. The guidewire 50, the shaft 12 and the catheter 14 can be longitudinally translated in coupled or uncoupled fashion, simultaneously or sequentially. By way of example, some or all of these devices can move with respect to some or all of the other devices.

Figure 8A:
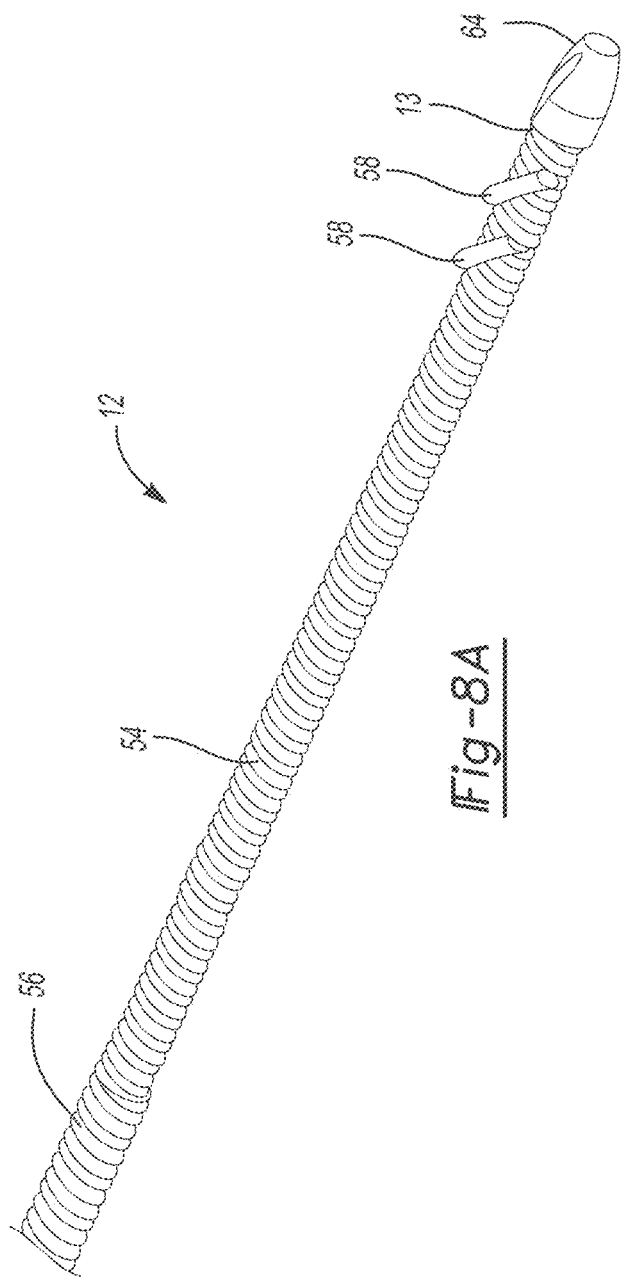
FIG. 8A is a perspective view of a flexible shaft according to some embodiments of the present teachings.
Figure 8B:
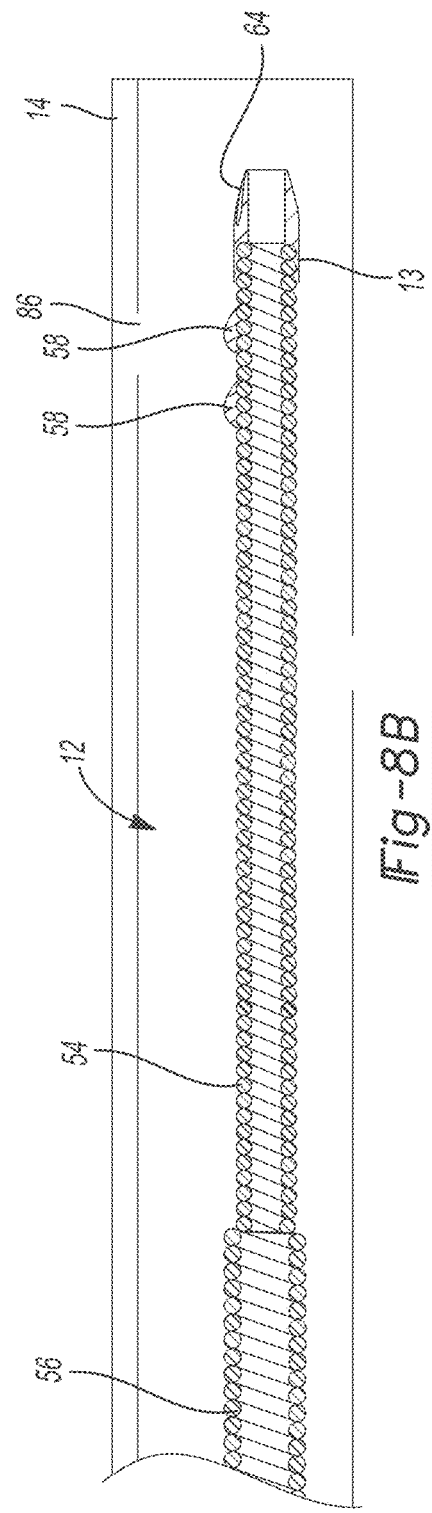
FIG. 8B is a side view of the flexible shaft of FIG. 8A disposed in a catheter according to some embodiments of the present teachings.
Figure 11A:
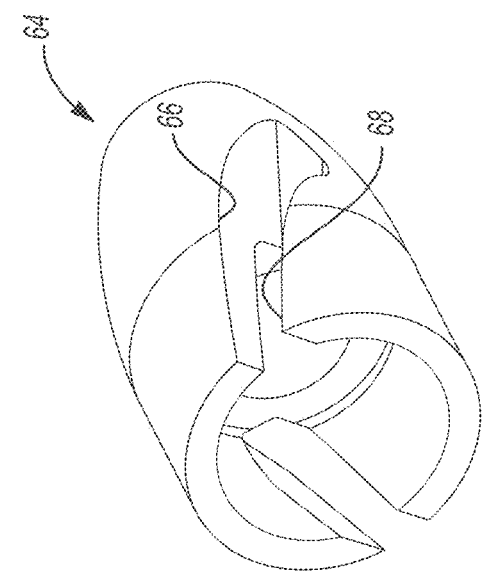
FIGS. 11A-11F are perspective views and end views of shaft tips for use with the flexible shaft according to some embodiments of the present teachings.
Figure 11B:
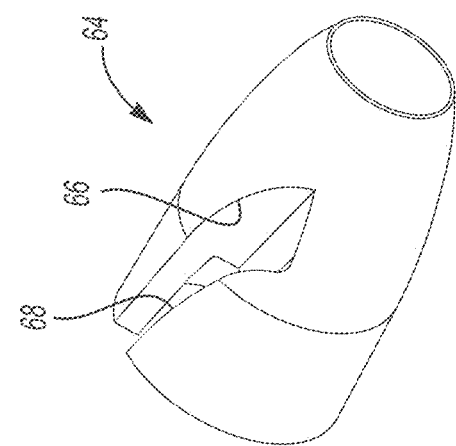
Figure 11C:
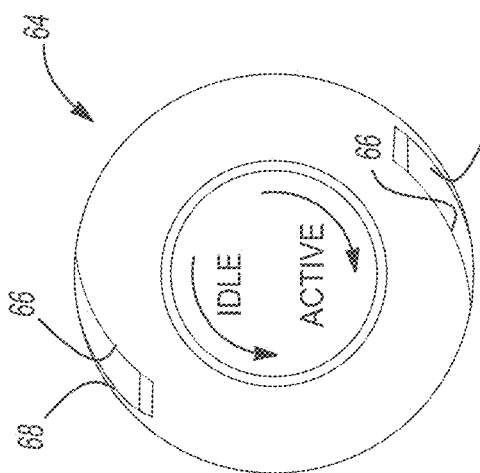
Figure 11D:
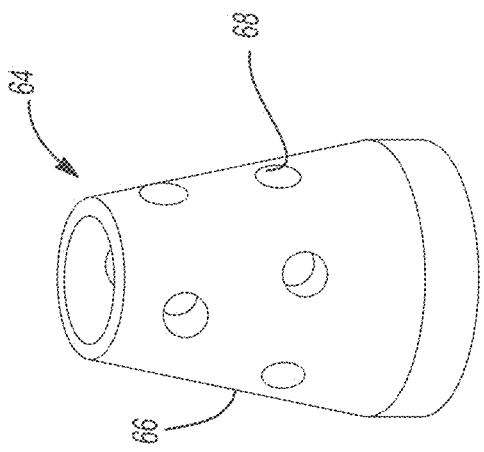
Figure 11E:
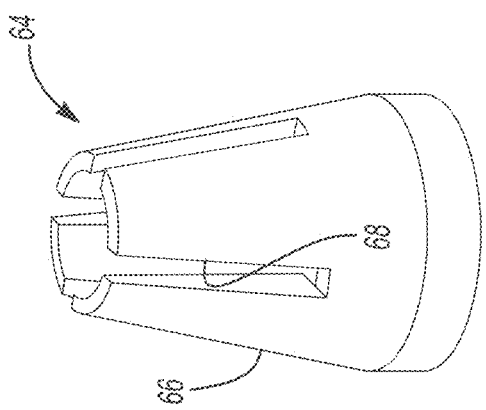
Figure 11F:
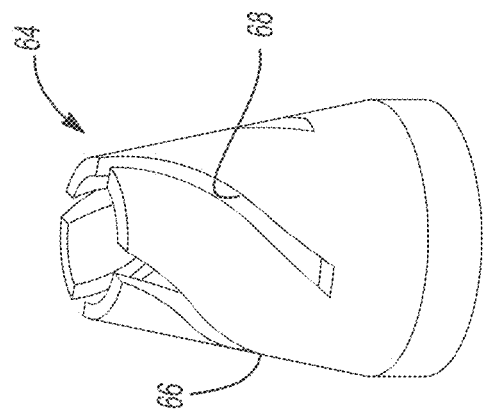
Figure 16B:
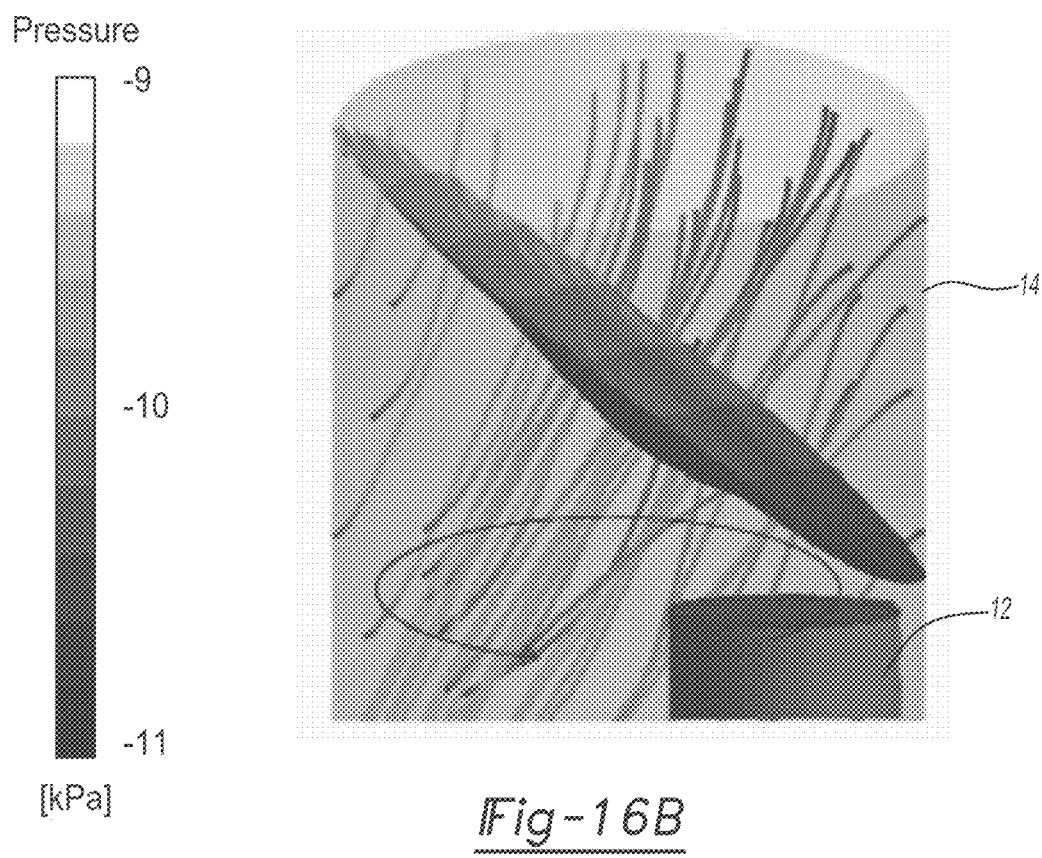
FIG. 16B is a pressure gradient graph illustrating the pressure gradient created within the catheter during thrombectomy.

After the aspiration catheter 14 is placed in the target, generally in proximity or within the clot mass, in the preferred embodiment the shaft 12 is shielded within the catheter 14, the guidewire 50 at least partially removed from the shaft lumen and the shaft 12 actuated by the drive system 32 as a "thrombectomy element" to generate a hydrodynamic vortex with a steep oblique pressure gradient, as shown in FIG. 16B. In some embodiments, as illustrated in FIGS. 8A-8B, flexible shaft 12 can be composed of multiple segments with different diameters, winding combinations, and/or braiding combinations. That is, flexible shaft 12 can comprise a first segment 54 and a second segment 56 (or additional segments). This allows flexible shaft 12 to be optimized for key parameters, such as torsional strength at the proximal end, flexibility at the distal tip, and contraction/elongation tendency of the shaft during navigation and high speed rotation (acts like a spring that can wind up, tightening and shortening the shaft 12, or unwind, elongating the shaft 12). In some embodiments the windings of shaft 12 are in opposite directions. In some embodiments, flexible shaft 12 comprises a larger diameter wind at the proximal end for torsional strength (in a preferred embodiment for a catheter with ID between 0.060"-0.070", the shaft 12 OD is between 0.026-0.040" with an ID of between 0.016-0.024" and a bending stiffness of approximately between 50 N mm^2 and 5000 N mm^2, where bending stiffness is defined as Young's modulus multiplied by the area moment of inertia of the flexible shaft 12) and a smaller diameter wind at and near the distal tip (typically between 0.026-0.034" OD with an ID of between 0.016-0.024" and a bending stiffness of approximately between 5 N mm^2 and 50 N mm^2) to help navigate through tortuous vessels. This lower bending stiffness distal length preferably extends between 0.5"-20" from the distal tip 13 of flexible shaft 12. It should be appreciated, as illustrated in FIG. 8C, that multiple shaft 12 segment configuration can be achieved by varying the cross-sectional size of the wire used to construct flexible shaft 12 from a diameter dp to a diameter dd, where diameter dp is larger, smaller, or different than diameter dd. Moreover, multiple layers of windings can be added to achieve various torsional and bending stiffness (see FIG. 8D). Furthermore, different materials can be used to achieve different shaft stiffness. These materials are commonly stainless steel or nitinol. Centerless grinding can also be used to reduce the outer diameter of flexible shaft 12 in certain sections to reduce the stiffness of that shaft segment. The shaft 12 can be a combination of coiled or braided metal such a nitinol or stainless steel and a plasticto form a plastic/metal composite. Lined braided shaft constructed with inner liner, braid, and the outer jacket can be used to provide required lubricity, torque transmission, fatigue resistance, pushability, steerability, and deformation and kink resistance. In this design, jackets of different polymers and thicknesses can be added to optimize torsional strength and bending stiffness. This can provide good torque transmission for rotational motion and also reduce friction between different elements in the telescoping system. The braiding/coils can also be raised up from the surface of the shaft to minimize the contact surface between the shaft and catheter(s) surrounding it. Shaft 12 can also be comprised of longitudinal fibers and fibers included in the coiling or braiding, for example of Kevlar, to prevent shaft elongation or separation in the event of shaft fracture. Polymer jacket and liners can also be included in the shaft 12 to prevent shaft separation in the event of wire fracture.

The outer diameter of flexible shaft 12 is preferably 20-80% of the inner diameter of aspiration catheter 14. Larger shafts 12 tolerate higher torque and bending force during thrombectomy and facilitate atraumatic coaxial advancement of the catheter 14. However, larger shafts 12 tend to cause drop in vacuum power and flow and may not advance easily over a guidewire 50 into the intravascular space during navigation. Smaller shaft 12 may navigate easier and minimize vacuum power loss although may not provide enough structure for coaxial advancement of catheter 14 or resist the torque load needed for vortices generation. Furthermore, higher torque and strength can be obtained by increasing the pick count and using larger diameter braid wire, although these will translate into higher stiffness and decrease flexibility.

In some embodiments, the same shaft 12 can have different zones to optimize torque resistance and rotational energy by a combination of features described herein. These zones can be created by welding, gluing, grinding, braiding, including jackets and liners, or other methods known to those skilled in the art. The changes in shaft design can be a continuous transition, a step-wise transition, or a combination of both. For example, at the base of flexible shaft 12 closest to the drive system 32, the winding of flexible shaft 12 can be very tight and potentially include a larger diameter wire and/or stronger jacket to help resist to the high torsional forces that are typically experienced at that location. Then, toward the distal end of flexible shaft 12, the winding of flexible shaft 12 and/or diameter of flexible shaft 12 and/or the jacket can be progressively diminished as smaller torsional forces are typically experienced near the distal end. This can act to enhance the flexibility and/or diminish flexible shaft 12 diameter while optimizing delivery of rotational energy to enable thrombectomy. In some embodiments, the jacket can be very thin or absent at least partially in the distal end of the flexible shaft 12 to uncover braid or coil texture to generate hydraulic features and interact with clot 100.

In some embodiments, flexible shaft 12 can be a continuous structure or can be formed by multiple segments. These segments can be connected to one another using, for example but not limited to, adhesives, welding, liners, or other joints that allow transmission of rotational forces.

The coiling density (coils/length/number and thickness of filars) of flexible shaft 12 can be different within different flexible shafts or along the length of the same shaft. In one embodiment there are between 3 and 12 filars with a thickness between 0.003-0.008". Typically, a larger filar count and larger filar thickness correspond to a stiffer and stronger shaft whereas a smaller filar count and a smaller filar thickness correspond to a more flexible and compliant shaft with lower bending stiffness. Additionally, a shaft with a larger outer diameter will typically have higher stiffness and torsional strength when compared to a shaft with a smaller outer diameter.

Higher torque and strength can be obtained by increasing the pick count and using larger diameter braid wire of the shaft 12, although these will translate into higher stiffness and decrease flexibility. In some embodiments, the wire size is 0.001-0.006" with a pick per inch of 20 to 600.

The cross-sectional design of flexible shaft 12 can be of a variety of different geometrical shapes, with examples of shapes including but not limited to circular, triangular, square and others. The cross-sectional design of flexible shafts can be different within different shafts or along the length of the same shaft. Therefore, it should be recognized that flexible shaft 12 (and catheter 14) do not need to have constant diameter along the total length of the device. In some instances, it can be beneficial to increase shaft and catheter diameter in the proximal end where high strength and pushability, or the ability for an object to be pushed/advanced without kinking or looping, but less flexibility is required. In one embodiment the outer diameter of the proximal end of flexible shaft 12 is approximately 0.036" with approximately 8 filar windings while the distal end is approximately 0.032" with 4 filar windings. In other instances, it can be beneficial to increase the diameter of catheter 14 toward the distal end to enhance vacuum efficiency and thrombectomy efficacy.

In some embodiments, the flexibility and torque resistance of flexible shaft 12 can be modified by changing diameter, material, geometric, jacket and braiding features of flexible shaft 12 and/or by introducing a guidewire 50 with different stiffness within flexible shaft 12.

In some embodiments, flexible shaft 12 is made of one or more metals, such as stainless steel and/or nitinol. It can be made through winding and/or braiding filament around a mandrel to produce a hollow shaft. The shaft 12 preferably includes a hollow channel to enable a guidewire 50 to be coaxially advanced within the flexible shaft 12 for system navigation, while simultaneously achieving sufficient torsional strength to resist breaking during use. In some embodiments, a polymer liner is included to provide a high degree of lubricity on the inner channel to facilitates the passage of a guidewire 50 or other devices through the lumen.

In some embodiments, flexible shaft 12 can be composed of multiple lumens that are either connected, un-connected, or a combination thereof to one another. As an example, there can be three shafts, each with their own lumen, that are combined to form an additional lumen where a guidewire can be slid through.

In some embodiments, the shaft 12 can be disposed and advanced into the vasculature without an internal guidewire 50. This shaft 12 can be steerable and, in some embodiments, can have a pre-formed shaped.

In some embodiments, the shaft 12 can acquire a shape after removal of the inner guidewire 50 or by unsheathing from a surrounding sleeve 45, or can be linear and acquire a shape after introduction of the guidewire 50. In some embodiments, as illustrated in FIGS. 8A-8B and 9A-9F, flexible shaft 12 comprises one or more hydraulic inducing features 58 that enhance hydraulic forces during rotation of flexible shaft 12. Hydraulic enhancing features 58 can include, but are not limited to, fins, bumps, ridges, and surface micro features, either along the entire shaft of flexible shaft 12, near distal end 13 of flexible shaft 12, or attached to distal end 13 of flexible shaft 12. In some embodiments, hydraulic enhancing features 58 increase hydraulic force to enhance destruction and/or maceration of clot 100.

In some embodiments, as illustrated in FIGS. 8A-8B, 9A-9F, and 10A-10D, flexible shaft 12 comprises one or more eccentric features 60 to further induce translational motion of flexible shaft 12 to enhance the thrombectomy mechanism. It should be understood that in some embodiments hydraulic enhancing features 58 and eccentric features 60 may be the same feature performing both functions. These eccentric features 60 can be in the form of an eccentrically wound shaft, an eccentric mass fixed to part of flexible shaft 12, an eccentric tip on flexible shaft 12, or a combination thereof. An ideal eccentric feature 60 will be minimal in size so as to not significantly decrease the flexibility of flexible shaft 12 while still being large enough to induce translational motion in flexible shaft 12 during rotation. In addition, it should ideally be tapered and have an atraumatic configuration to enable safe intravascular navigation of the shaft, unless a sleeve 45 is used to shield cutting and/or abrasive surfaces. This eccentric feature can be of any length and disposed at any point or several points along the length of flexible shaft 12, and may even extend beyond the distal most end of flexible shaft 12. The eccentric feature could be made of a radiopaque material such as tantalum or Platinum Iridium. The eccentric mass can be single or multiple. In a typical device for removing clots in large cerebral artery, the eccentric mass can have a thickness of 0.001 to 0.020 inches, a length of 0.1 mm to 5 millimeters, and consist of a full ring or partial ring. The eccentric mass can be completely embedded within the jacket and outer liner of the shaft leading to atraumatic shape and surface for navigation with functional eccentricity for thrombectomy.

Eccentric features 60 can as well have cutting geometries and thrombectomy enhancement features, although not all thrombectomy enhancing features are necessarily eccentric components.

In another embodiment, an off-center channel at least partially along the shaft 12 or the shaft tip 64 can create eccentric features.

Flexible shaft 12 can also have features including but not limited to an abrasive coating, surface micro features and patterning to augment friction between flexible shaft, the fluid environment 12 and clot 100. This can translate into stronger hydrodynamic waves and grasp of clot 100 by flexible shaft 12 resulting in enhanced corkscrew inward traction of clot 100 into catheter 14.

Flexible shaft 12 can also have features including but not limited to a lubricious coating in the outer and/or inner lumens at least partially along its length to reduce friction between the shaft 12, the guidewire 50 and the catheter 14.

Flexible shaft 12 can be advanced or withdrawn to optimize its position into the maximal thrombectomy zone 74 to optimize the interaction between shaft and clot 100 in the engagement zone. In addition, it can be completely withdrawn from catheter 14 and exchanged if needed.

The advancement or retraction of flexible shaft 12, guidewire 50, and/or catheter 14 can be enhanced by very low speed rotation (typically <200 rpm), vibration or oscillation (typically greater than 2 Hz) of flexible shaft 12 by the user's hand or a drive system 32. It should be noted that this operation mode is for device navigation. For thrombectomy, the preferred embodiment is with flexible shaft 12 fully contained within catheter 14 and rotated at higher speeds as set forth herein.

In some embodiments, flexible shaft 12 can be navigated into the vasculature as described herein, and then used as scaffolding to advance a catheter over-a-shaft. The advancement or retraction of catheter 14 can be enhanced by very low speed rotation (typically <200 rpm), vibration, or oscillation (typically greater than 2 Hz) of catheter 14 by the user hand or a motor (same or different motor than motor causing high speed rotation for vortex generation). The same shaft can have different zones to optimize scaffolding by a combination of features mentioned above.

In some embodiments, as illustrated in FIGS. 8A-8B and 11A-11F, flexible shaft 12 comprises a shaft tip 64 that is connectable, coupled, or otherwise extending from distal end 13 of flexible shaft 12. In some embodiments, shaft tip 64 can be rounded and have smooth atraumatic edges 66 during navigation in the vessel, and have one or more sharp edges 68 during thrombectomy mode. This can be achieved by, but not exclusively by: 1) including grooves in an angled position, resulting in two edges, one sharp and the other dull (see FIGS. 11A-11C). When flexible shaft 12 rotates clockwise, the sharp edge moves forward to engage and cut clot 100 (active thrombectomy mode). When flexible shaft 12 rotates counter-clockwise (navigation mode) the sharp edge moves away from the surrounding tissue facilitating shaft advancement into the vascular lumen by low-speed rotation. Shaft tip 64 can be otherwise rounded or smooth to facilitate advancement with the introduction of the guidewire 50 for navigation mode. In some embodiments, shaft tip 64 includes a lumen in the tip that is co-axially oriented to the main longitudinal axis of flexible shaft 12 with a taper that varies in steepness through the circumference of the tip gradient, resulting in a smooth and rounded tip with the introduction of the guidewire 50 for navigation mode, and a "spoon" notch in flexible shaft 12 tip for clot 100 maceration upon wire removal. It should be noted that the latter two embodiments, or any variations of such embodiments, create an off-center mass that will enhance orbital movement of flexible shaft 12 and vortex generation upon rotation at high speed. As the outer diameter of guidewire 50 is smaller than shaft inner diameter, the off-center mass can be enhanced by shifting the lumen of the tip away from the longitudinal axis of flexible shaft 12. In some embodiments, thrombectomy enhancement features can be cutting geometries, surface features, and deployable element of shaft 12. By advancing or withdrawing sleeve 45 over the shaft during navigation or thrombectomy modes: 1) cutting geometries and surface features can be shielded or exposed; 2) deployable elements can be folded or unfolded; 3) pre-shaped configurations can be rectified or released. The latter configuration can be as well achieved by removing the guidewire 50. In some embodiment, the thrombectomy enhancement features can be reduced by introduction of guidewire 50.

In one embodiment, cutting geometries may have a given rake angle ($\alpha$), inclination angle ($\lambda$), cutting speed (v), as illustrated by point A (see FIGS. 26A-26D). A is defined by a radius r and an offset (e). The inclination angle at point A is $$\lambda(r) = \sin^{-1}\frac{R_o - e}{r}, R_I \leq r \leq R_O,$$

where Ro is the OD of the cutting tool. In practice, high $\lambda$ enables more effective cutting of compliant tissue, including thrombus material. In some embodiments, introduction of guidewire 50 diminishes the cutting geometry and results in a smooth and rounded shaft tip 13 for navigation mode.

In some embodiments, the surface may have features, such as micro-dimples, micro-indentations, micro-grooves or the combination. Those features create unsteady microscale vortices and increase the turbulence intensity near the shaft. This creates local large pressure fluctuation and generates impact on the thrombus material that may lead to micro-damages to the thrombus material. Those features also increase the ability of the shaft dragging the thrombus material.

In some embodiments, deployable elements 59 may be added to facilitate removing of thrombus material (see FIGS. 27A-28B). Before deployed, the deployable element has minimum cutting power. Once deployed, the element's outer diameter increases, and the removing mechanism is enhanced. The deployable element can have the above-mentioned cutting geometries and surface features and the combination of them. In some embodiments, the deployable element can be made of shape-memory alloy such as nitinol. The deployable element will deploy and or expand and recover its original shape upon unsheathing of the shaft. In some embodiment, as illustrated in FIGS. 27A-28B, during thrombectomy the hydraulic enhancing features 58 can be deployed by high speed rotation of the flexible shaft 12 and interaction with the clot mass 100 and fluid (see FIGS. 28A-28B), and fold back in an undeployed resting position (FIGS. 27A-27B) upon sufficient decrease in the rotational speed for low-profile navigation. In some embodiment, the deployable element can be made of radiopaque material and function as well as fluoroscopic marker.

In some embodiments, the shaft 12 can be shorter than the telescoping system and disposed within the aspiration catheter 14 in a distal location. The shaft 12 can be moved longitudinally in a coupled or uncoupled fashion from the aspiration catheter 14. The movement of the shaft 12 can be achieved by mechanical coupling of the shaft to one or more wires controlled by the actuator module or the operators hand. The wire or wires are connected distally at least partially into the proximal end of the shaft and are disposed inside, outside or within the walls of the aspiration catheter 14 or a combination of it. The wire or wires are connected proximally to a slider within an actuator or directly operated by the operator's hands. The wire can be advanced towards the catheter, which causes the shaft to emerge from the catheter and advance into the vascular lumen as a navigation element (this can be supported by the use of a co-axial guidewire if needed inside the shaft). In this position, the shaft 12 provides scaffolding for catheter advancement to target during navigation mode. The length of shaft 12 deployment varies depending on the vascular anatomy that has to be navigated but typically is between 1 cm and 30 cm. After advancing the catheter 14 to target, the shaft 12 can be retracted into the catheter lumen 14 by withdrawing the wire and can be actuated to generate vortices forces for thrombectomy. The actuation of the shaft 12 can be driven by mechanically transmitting the rotation of one or more wires to the shaft through a system of gears and belts or alike. In this embodiment, the wire is coupled to a motor capable of generating enough rotational speed to generate vortices forces by transmitting enough rotational energy to the shaft 12. In another embodiment, the shaft 12 rotation can be generated by delivering pressurized solutions to the shaft featuring blades or fins or grooves. The wire adjusting the position of the shaft can be a solid or hollow, monofilament, coil or braid or any combination thereof. The telescope system in this embodiment can improve vacuum efficiency and flow by reducing the extend of shaft 12 disposed within the suction catheter 14, and optimizes torque transmission while reducing wear and tear by disposing a wire in the segments of the telescope system traversing tortuous anatomy and enabling vortices generating forces by the shaft in the regions of the catheter of maximal need for thrombectomy, typically the most distal 5 cm.

Catheter

In some embodiments, catheter 14 is configured to be navigated through vascular geometries, and is made from pliable material. In some embodiments, catheter 14 is made sufficiently stiff to not collapse under suction force or kink upon small bending radius. In some embodiments, catheter 14 is structurally reinforced to prevent kinking of the lumen with bending. In a typical embodiment, a polymer lined braided catheter with inner liner, braid, and outer jacket is used to achieve lubricity, torque, pushability, steerability, and kink resistance. For treatment of stroke due to large vessel occlusion, inner diameter of catheter range 4-6 French, although smaller and larger sizes can be used depending on the application.

Figure 7D:
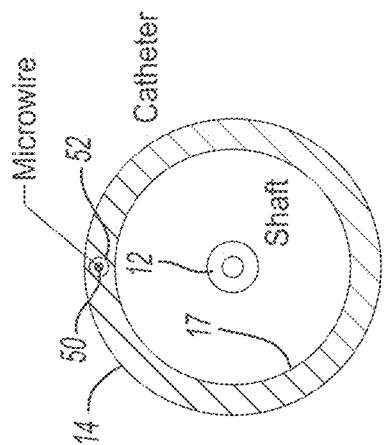
FIGS. 7A-7D are schematic end views illustrating a flexible shaft disposed within a catheter according to the principles of the present teachings.
Figure 7C:
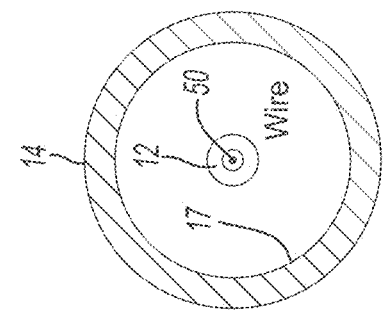
Figure 7B:
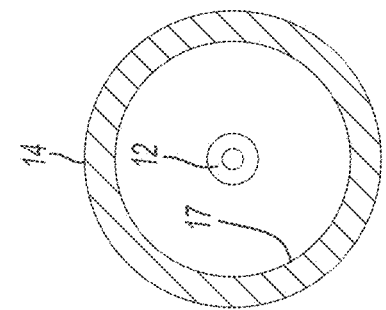
Figure 7A:
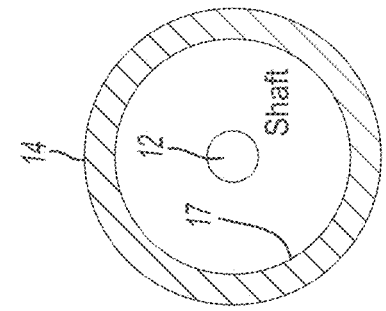

In some embodiments, wall surface 17 of catheter 14 has a hollow channel that spans the length of catheter 14 and opens distally. This hollow channel enables a guidewire 50 to be disposed within the wall of catheter 14 (FIG. 7D). This guidewire 50 can optionally be steerable and be advanced outside the distal end of catheter 14 into the vascular lumen to facilitate and direct advancement of catheter 14 into the mass of clot 100 and into the target vessel, both before, during, or after mechanical thrombectomy by powering flexible shaft 12 in catheter 14 as described herein.

Figure 12:
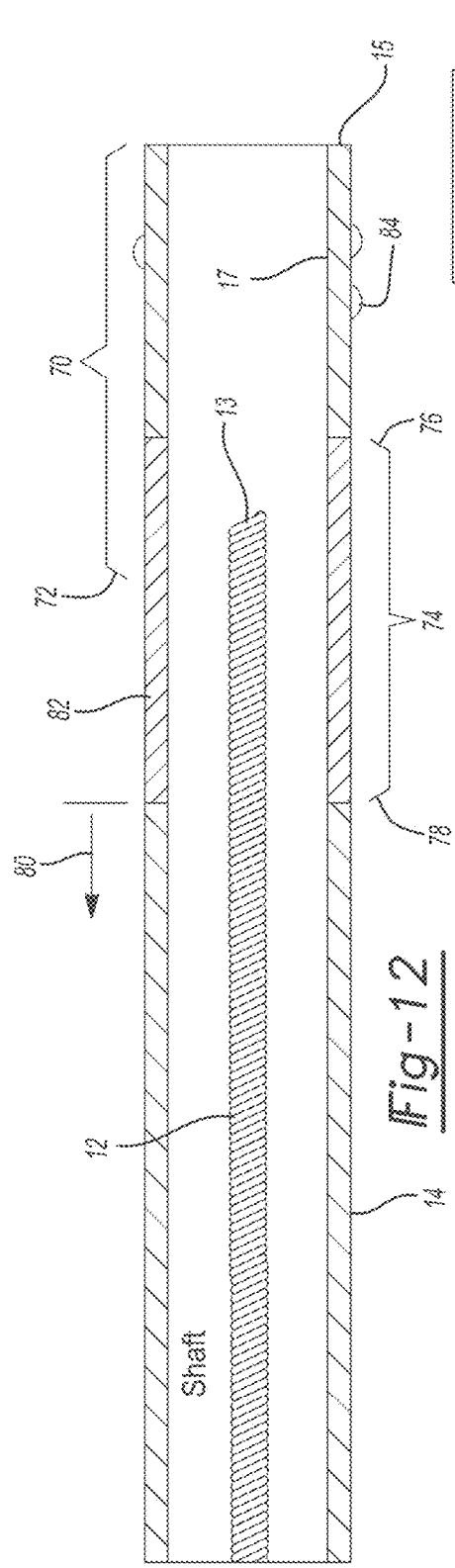
FIG. 12 is a partial cross-sectional view of the catheter and flexible shaft according to some embodiments of the present teachings.

In some embodiments, as illustrated in FIG. 12, the combination of flexible shaft 12 and catheter 14 can define one or more zones that are particularly adapted and configured to perform mechanical thrombectomy upon clot 100. As disclosed herein, flexible shaft 12 is positioned within catheter 14 and is rotating at a very high speed to create hydrodynamic vortices and corkscrew movements to further disrupt clot 100. Generally, a clot engager zone 70 is located from distal end 15 of catheter 14 and proximally extends within catheter 14 to a location 72 proximal from distal end 13 of flexible shaft 12. A maximal thrombectomy zone 74 is further proximally located relative to clot engager zone 70, although maximal thrombectomy zone 74 can overlap clot engager zone 70 to some, all or no extent. Maximal thrombectomy zone 74 can be bound at a distal end 76 (extending distally past distal end 13 of flexible shaft 12) and a proximal end 78 (extending proximally relative to distal end 13 of flexible shaft 12). An anti-clog zone 80 is still further proximally located relative to maximal thrombectomy zone 74 and generally extends within catheter 14.

In some embodiments, the distal most segment (e.g. clot engager zone 70) of catheter 14 may be at an angle to the longitudinal axis of catheter 14.

Clot engager zone 70 anchors clot 100 to catheter 14 optimizing the thrombectomy mechanisms described herein. In addition, clot engager zone 70 maintains clot 100 anchored to catheter 14, minimizing release of free fragments. The combination of shaft orbital translation, shaft transverse vibration, and torsional indraft pull following a corkscrew pathway due to pressure gradient, flow shear, and contacting force between flexible shaft 12 and contacting clot 100, and vacuum overlapping at clot engager zone 70 provides a synergetic thrombectomy milieu that is safely contained within catheter 14. In addition, clot engager zone 70 provides a safety buffer zone to allow the periodic elongation and contraction of flexible shaft 12 when it is rotated at high speed, such that flexible shaft 12 is not disposed on the outside of catheter 14 where it can potentially cause damage to the blood vessels or body cavity.

In some embodiments, at least the maximal thrombectomy zone 74 of catheter 14 will have a reinforced segment 82 to increase the structural resistance of catheter 14 to forces and energy transmitted by the motion of flexible shaft 12, as shown in FIG. 12. This segment 82 can be coated with anti-abrasive material, have reinforcing coils and/or bands. In some embodiments, distal end 15 of catheter 14 and maximal thrombectomy zone 74 can be structurally reinforced to prevent collapse of the lumen of catheter 14 with vacuum.

In some embodiments, at least the maximal thrombectomy zone 74 of catheter 14 and flexible shaft 12 comprise fluoroscopic markers to aid in the positioning of distal end 13 of flexible shaft 12 and/or the catheter 14 in optimal position for activation. In some embodiments, these fluoroscopic markers can be designed to align the thrombectomy components to indicate a range of acceptable tolerances in shaft positioning. In some embodiments, the fluoroscopic marker of a catheter 14 can be ring shaped and disposed in the region of maximal thrombectomy. In this embodiment, the fluoroscopic marker of the shaft can be an incomplete ring but longer than that catheter marker. In this embodiment, the appropriate alignment of both fluoroscopic markers would create a "T" detectable by fluoroscopy. In other embodiments, the fluoroscopic marker of the shaft is complete but smaller than the catheter marker, leading to fluoroscopic double ring sign when the catheter and shafts are appropriately aligned. n some embodiments, fluoroscopic markers, CT and MRI markers can be provided in any portion of catheter 14, guidewire 50, sleeve 45, and/or flexible shaft 12.

In some embodiments, distal end 15 of catheter 14 includes one or more uneven features 84 disposed thereon (e.g. rounded bumps). In some embodiments, features 84 can be along the same direction as the long axis of catheter 14. Features 84 help to penetrate and break apart clot 100 due to concentrated areas of high shearing force as clot 100 is dragged inward into maximal thrombectomy zone 74 following a corkscrew path.

In some embodiments, catheter 14 can have one or multiple inner and outer diameters and have multi-durometer construction.

In some embodiments, catheter 14 can have windows in the wall to facilitate clot removal.

In some embodiments, the catheter distal end 15 can be beveled to improve the contact of the clot to the catheter the shaft.

Figure 13A:
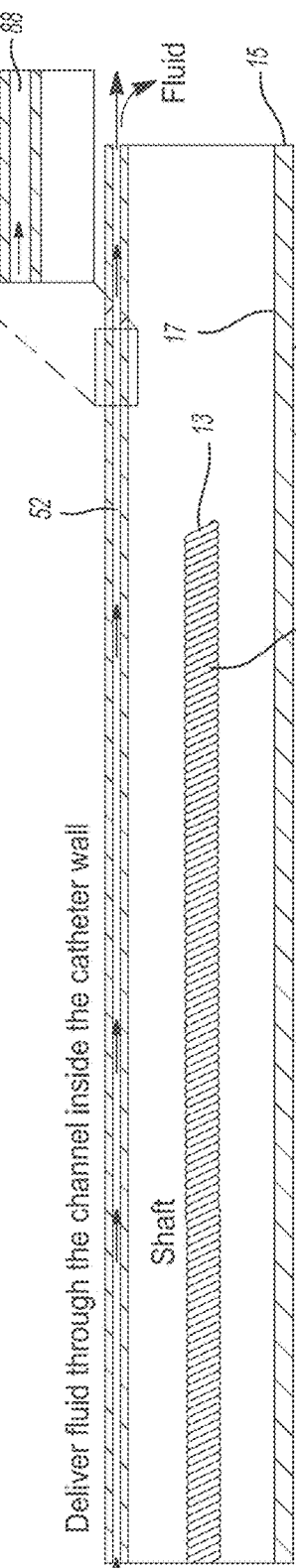
FIGS. 13A-13C are partial cross-sectional views of the catheter and flexible shaft having fluid and/or guidewire delivery systems according to some embodiments of the present teachings.
Figure 13B:
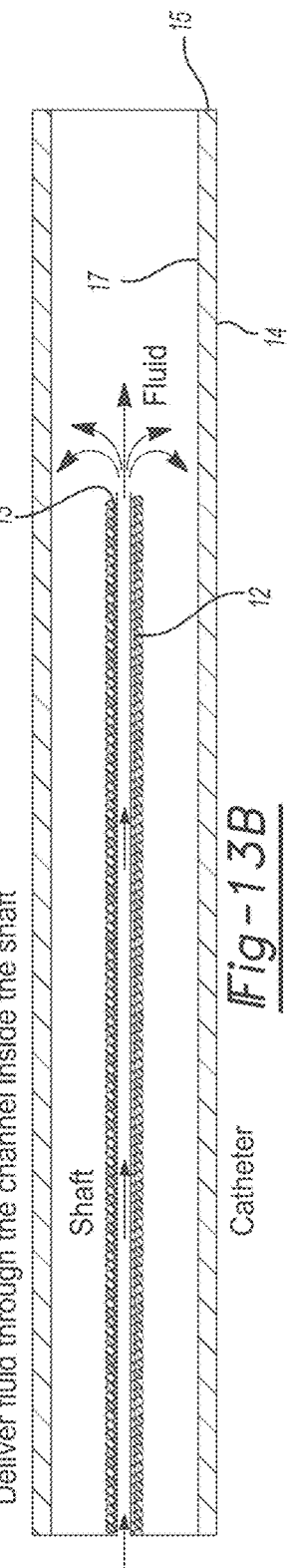
Figure 13C:
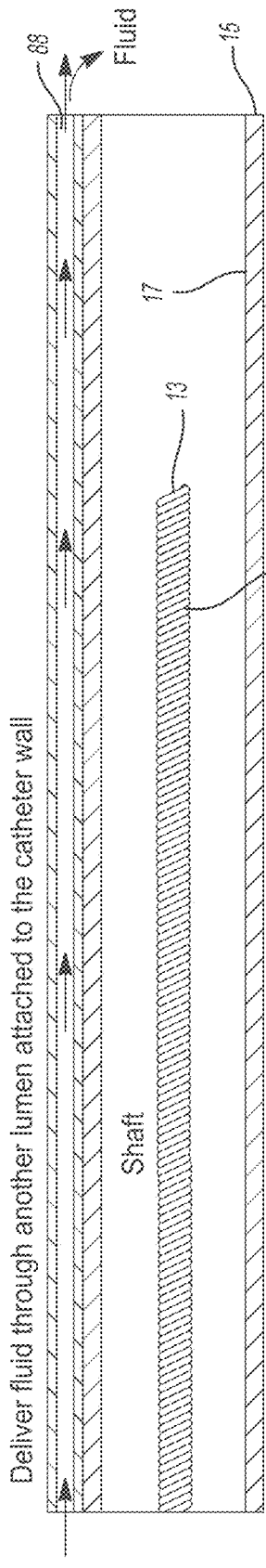
Figure 14A:
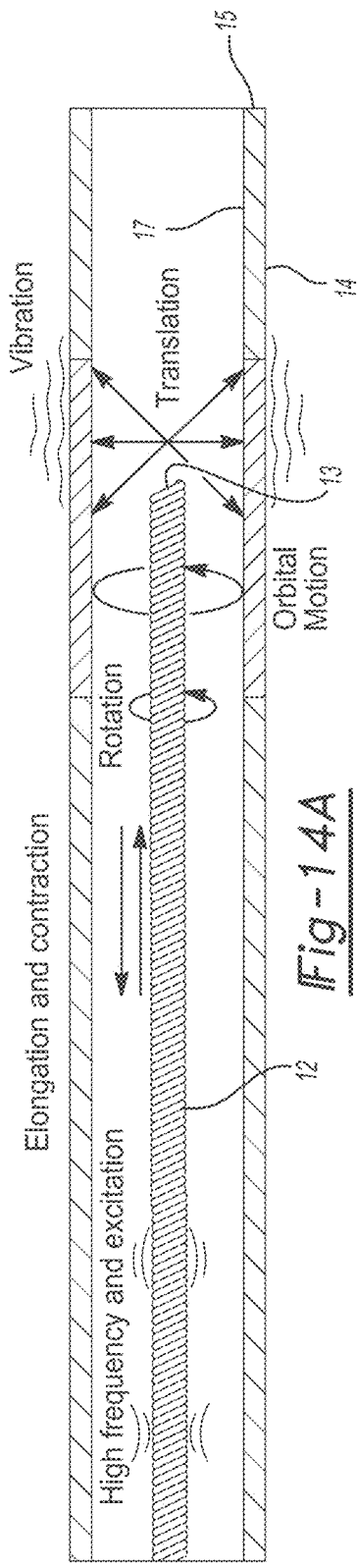
FIGS. 14A-14B are a partial cross-sectional views of the catheter and flexible shaft illustrating the motion responses of the catheter and flexible shaft during thrombectomy according to some embodiments of the present teachings.
Figure 14B:
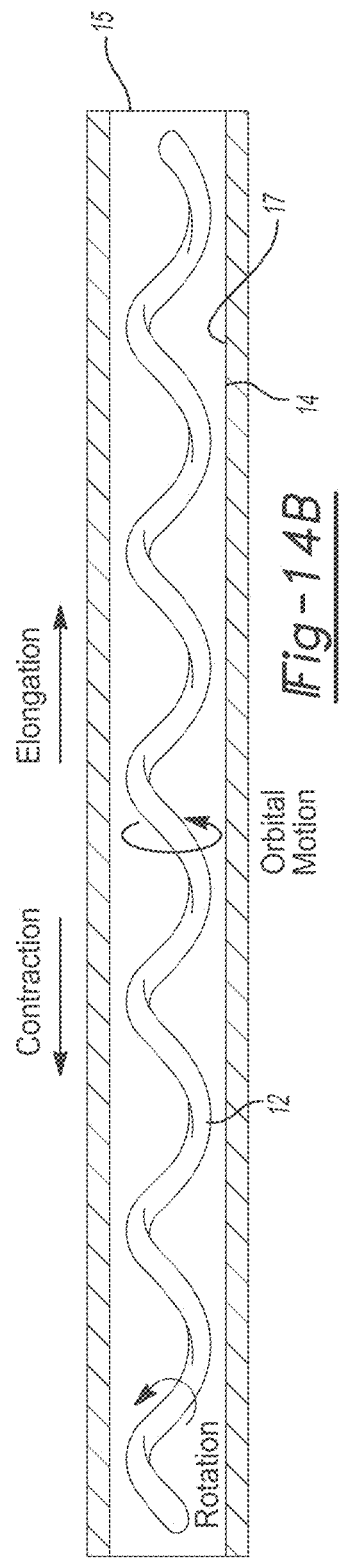
Figure 15A:
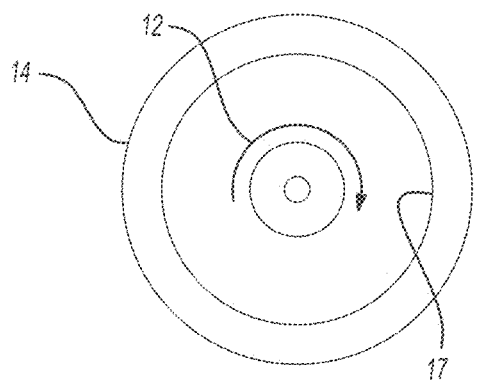
FIGS. 15A-15D are schematic end views illustrating motion of the flexible shaft disposed within a catheter according to the principles of the present teachings.
Figure 15B:
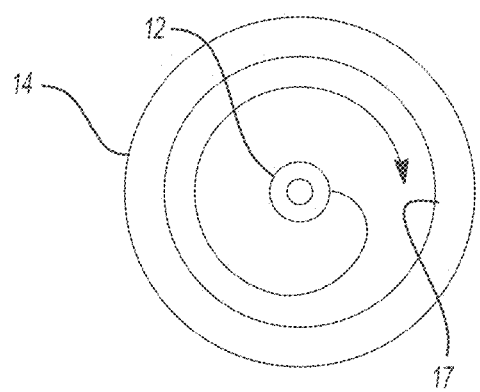
Figure 15C:
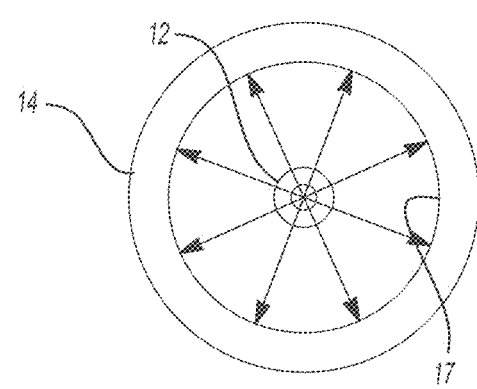
Figure 15D:
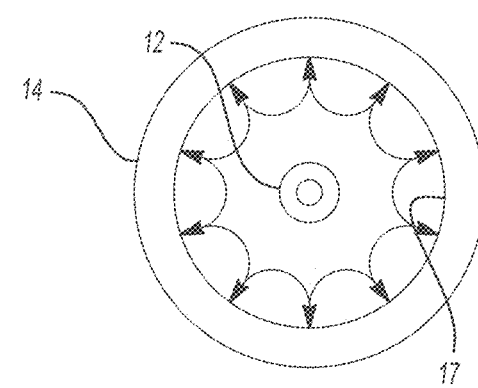

In some embodiments, as illustrated in FIGS. 8B and 13A-13C, catheter 14 may have accessory lumen, channel, or holes 86 in the wall to allow fluid (saline solution, blood, medication, etc.) to fill the lumen of catheter 14 preventing cavitation upon vacuum and maintain the environment needed to generate hydrodynamic forces, and aid in removal of material. Moreover, in some embodiments, as illustrated in FIGS. 7D, 8B, and 13A-13C, catheter 14 may have accessory lumen or channel 88 throughout the totality or part of its extension to allow guidewire 50 or other wire to be disposed within for navigation or to infuse solutions or medications. Particularly, as illustrated in FIG. 13A, a channel 88 can be disposed within the sidewall of catheter 14 to deliver a fluid. As illustrated in FIG. 13C, channel 88 can extend along an ancillary channel of catheter 14. In some embodiments, the fluid can be delivered through the hollow interior of flexible shaft 12 (FIG. 13B).

In some embodiments, wall surface 17 of catheter 14 has a hollow channel that spans at least part of the length of catheter 14 and opens at the distal end of catheter 14, into the lumen of catheter 14, or a combination thereof. This hollow channel enables the advancement of a guidewire 50 to be used in monorail system, both during navigation mode of catheter 14 (with or without co-axial advancement over a shaft) and thrombectomy mode. In the latter option, flexible shaft 12 is rotating at very high speed inside catheter 14 causing clot 100 engagement and fragmentation while catheter 14 is advanced or pulled back over the monorail wire disposed in the vascular lumen, and not in contact with flexible shaft 12 (FIG. 8).

In some embodiments, wall surface 17 of catheter 14 has a hollow channel that spans at least part of the length of catheter 14 and opens at the distal end of catheter 14, into the lumen of catheter 14, or a combination thereof. This hollow channel enables the advancement of a distal embolization protection device, such as a net or filter, that can be advanced through clot 100 mass and: 1) be pulled back facilitating entrance of clot 100 into catheter 14; 2) remain distal to clot 100 to capture embolization particles and then be pulled back allowing these particles to be removed by catheter 14.

In some embodiments, wall surface 17 of catheter 14 has a hollow channel that spans at least part of the length of catheter 14 and opens at the distal end of catheter 14, into the lumen of catheter 14, or a combination thereof. This hollow channel enables the advancement of an occlusive device, such as a balloon, which can be advanced through clot 100 mass and then: 1) insufflated to prevent distal embolization by stopping anterograde flow, 2) be pulled back facilitating entrance of clot 100 into catheter 14.

In some embodiments, wall surface 17 of catheter 14 or flexible shaft 12 can have a hollow channel to deliver medication, cooling fluids or other agents toward the distal end of catheter 14.

In some embodiments, catheter 14 may have a flow occlusion mechanism, such as one or more balloons, near or at the distal end 15 to enhance suction force applied to the region of interest, reduce the pressure upon which the material needs to be removed, and diminish or stop flow minimizing distal embolism.

In some embodiments, catheter 14 includes a filter device for capturing undesirable material and removing it from the fluid flow.

Thrombectomy Forces

The rotation of flexible shaft 12 contained within catheter 14 induces key engagement and fragmentation mechanisms (see FIGS. 14A-14B, 15A-15D, 16A-16B, 19A-19G), such as, but not limited to:

a. Hydraulic forces created between flexible shaft 12 and the inner wall surface 17 of catheter 14 due to the rotation of flexible shaft 12 within catheter 14 and the induced uncoupled translational motion of flexible shaft 12 (see FIGS. 14A-14B) that fragments clot 100 within catheter 14.

b. The hydraulic forces created by high speed shaft rotation and orbiting coupled with vacuum generate a vortex with a steep pressure gradient obliquely oriented in the lumen of catheter 14 and rotating inside catheter 14 (see FIGS. 16A-16B).

c. This vortex generates a torsional indraft pull following an inward corkscrew pathway to further engage clot 100 into catheter 14 and create shear stress that is more effective than stand-alone vacuum to anchor, pull, and fragment clot 100 (see FIGS. 19A-19G).

d. The vortex also potentiates clot 100 engagement, fragmentation, and inward movement of the clot 100 proximally within catheter 14 due to the transformation of static friction between clot 100 and inner wall 17 to kinetic friction which tends to produce a lower resistive force between clot 100 and inner wall 17.

e. The high frequency excitation of flexible shaft 12 fragments clot 100 further and causes flexible shaft 12 to repeatedly hit the inner surface of catheter 14 (see FIGS. 15A-15D)). This creates a high frequency (typically 100 to 300 Hz), low amplitude vibration (typically 50 μm to 200 μm) of catheter 14 that aids in clot 100 disruption, indicated as the "vibration" in FIG. 14A.

f. The high-speed rotation of flexible shaft 12 in combination with the coiled or braided wire design of flexible shaft 12 induces a periodic elongation and contraction of flexible shaft 12 due to torsional vibration and unstable turbulent flow, indicated as the "elongating and contracting" in FIG. 14B. This dynamic forward and backward movement of a distal end 13 of flexible shaft 12 lengthens the zone 74 of maximal thrombectomy efficacy. By way of non-limiting example, periodic elongation and contraction can be within about 0.1 to 5 mm, based on shaft material, winding pattern, wire diameter, torsional modulus, vessel tortuosity, and the like.

g. The hydrodynamic forces generated by high speed rotation of flexible shaft 12 induces 3-dimensional corkscrew movement of flexible shaft 12, which swipes between inner wall surface 17 of catheter 14 and clot 100 surface. This minimizes static friction between clot 100 and wall surface 17 of catheter 14, de-attaching clot 100 from wall surface 17 of catheter 14, and enhancing clot 100 removal by transforming static friction to kinematic friction. It should be understood that the three-dimensional corkscrew configuration and movement of flexible shaft 12 is achieved upon application of high-speed rotational motion (typically greater than 10,000 RPM).

h. At rest, the flexible shaft 12 substantially defines a straight, linear profile, without the need for complex preformed shapes, such as angles, J's, sinusoids, and the like. In some embodiments, non-linear shapes of flexible shaft 12 at rest can be used in connection with the present teachings. These shapes can be fixed or acquired after removal of inner guidewire 50.

i. Static friction is substantially reduced or eliminated by the steep pressure gradient obliquely oriented in catheter 14 that rotates inside catheter 14 and extends throughout the lumen of catheter 14.

j. The movement of flexible shaft 12 also engages with clot 100 substance enhancing/accelerating the inward corkscrew path to further engage and fragment clot 100.

k. The same mechanisms described herein can occur from the distal end of the maximal thrombectomy zone 74 to the proximal end of catheter 14 with decreased intensity preventing the lumen from clogging, indicated as the anti-clog zone 80 in FIG. 12A.

l. Features on flexible shaft 12, such as but not limited to thrombectomy enhancing features and angled eccentric mass 58, 60 on distal end 13, can further act to pull clot 100 into catheter 14 by transmitting axial and tangential forces to clot 100.

In some embodiments, to enhance the axial force of the rotating shaft 12, magnets can be added the catheter 14 and flexible shaft 12 such that when flexible shaft 12 is rotated with respect to catheter 14, the poles of the opposing magnets periodically attract and repel one another. In some embodiments, one or more magnets can be included in any of the elements of the telescoping system to prevent the release of free magnetic fragments. In some embodiments, the system may include a reinfusion cannula to reintroduce the fluid removed from the patient back into the patient.

In some embodiments, to enhance the hydrodynamic force on the rotating shaft 12, hydrophilic coatings can be applied to shaft 12.

Sleeve

In some embodiments, a tri-axial telescoping system will be enhanced by the addition of a sleeve 45 to be disposed between flexible shaft 12 and catheter 14. This tetra-axial system may enhance both navigation and thrombectomy as described below.

In some embodiments, sleeve 45 is made from pliable material but sufficiently stiff to not collapse or kink upon small bending radius and entrap the inner flexible shaft 12. Sleeve 45 can be moved along the longitudinal axis of catheter 14 by a sleeve advancement slider 47 in a coupled or uncoupled fashion with shaft advancement slider 28. Sleeve 45 can have the following functions depending on the embodiment and configuration as detailed below.

In one embodiment, sleeve 45 can be selectively advanced beyond distal end of catheter and at least partially over flexible shaft 12, creating additional scaffolding to help facilitate the advancement of catheter to the desired position and decreasing the shelf between flexible shaft 12 and catheter. In this embodiment, sleeve advancement slider 47 can be coupled to shaft advancement slider 28 to enable synchronous movements of these two structures co-axially, and can be uncoupled anytime to move independently flexible shaft 12 or sleeve 45. Upon advancement of catheter 14 in the desired position, the guidewire 50 can be withdrawn into flexible shaft 12, flexible shaft 12 can be withdrawn inside catheter 14 and sleeve 45 can be withdrawn into catheter 14 exposing at least a part of flexible shaft 12 to enable the generation of thrombectomy forces upon high speed rotation.

Figure 25A:
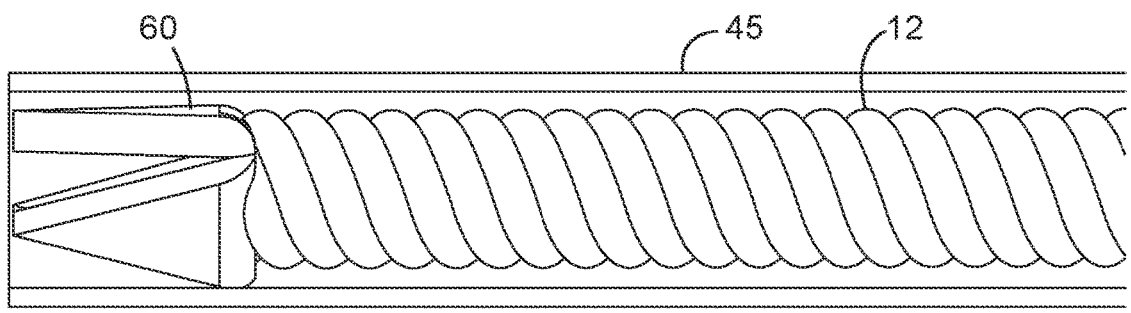
FIG. 25A is a side view illustrating a sheathed deployable element disposed on the flexible shaft and contained with the sleeve.
Figure 27A:
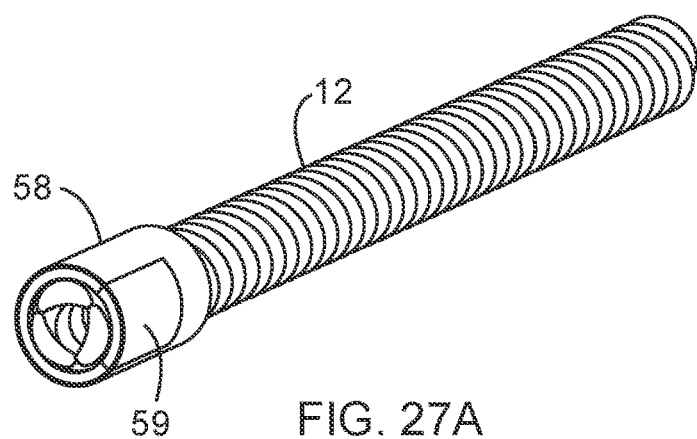
FIG. 27A is a perspective view of the flexible shaft having an enhancing feature deployable in response to high speed rotation of the flexible shaft illustrated in an undeployed position.
Figure 27B:
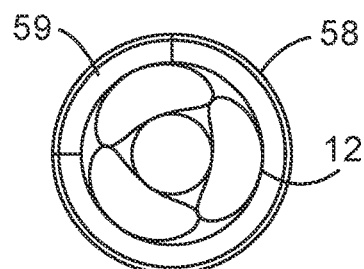
FIG. 27B is an end view of the flexible shaft and enhancing feature of FIG. 27A.
Figure 28A:
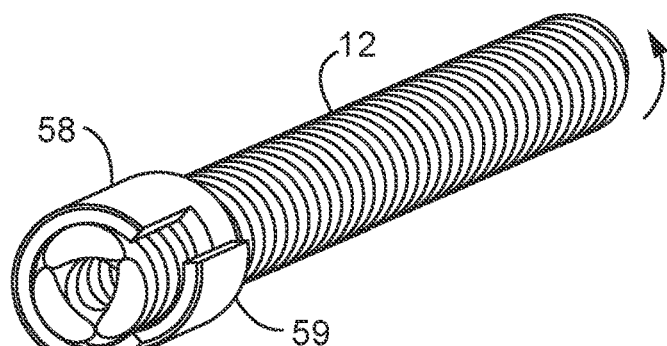
FIG. 28A is a perspective view of the flexible shaft having the enhancing feature deployable in response to high speed rotation of the flexible shaft illustrated in a deployed position.
Figure 28B:
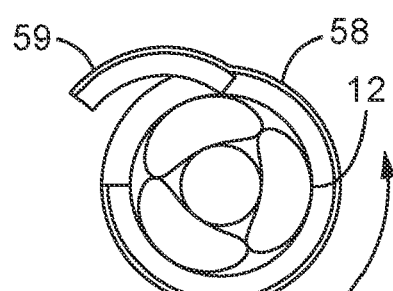
FIG. 28B is an end view of the flexible shaft and enhancing feature of FIG. 28A.

In some embodiments, as illustrated in FIGS. 25A-25B, sleeve 45 can be selectively advanced distally relative to flexible shaft 12 thereby shielding the thrombectomy enhancement features. This is convenient during the disposal or insertion of distal end 13 of flexible shaft 12 into the vascular bed during navigation mode as flexible, tapered, smooth and featureless configurations will minimize endovascular damage. In this embodiment, during navigation mode the sleeve 45 can be selectively advanced at least partially over flexible shaft 12 by uncoupled advancement of the sleeve slider 47 over a temporarily fixed shaft advancement slider 28. Upon advancement of catheter 14 in the desired position, the guidewire 50 can be withdrawn into flexible shaft 12, flexible shaft 12 can be withdrawn inside catheter 14 and sleeve 45 can be withdrawn further into catheter 14 exposing at least a part of the distal flexible shaft 12.

In some embodiments, the distal segment of sleeve 45 can be elastic to cinching over a guidewire when selectively advanced distally to the end of flexible shaft 12. This will shield any thrombectomy enhancing features of flexible shaft 12 and will create a more tapered configuration for enhanced navigation.

In some embodiments, during thrombectomy mode, sleeve 45 can be retracted to unsheathe thrombectomy enhancing features 60 of flexible shaft 12, unleashing the highly flexible shaft 12 to generate thrombectomy forces upon high speed rotation, and increase the available cross-sectional lumen to facilitate clot engaging and removal with maximal vacuum power.

In some embodiment, sleeve 45 can be selectively advanced along flexible shaft 12 to unload flexible shaft 12 of any clot debris. In another embodiment, flexible shaft 12 can be selectively withdrawn further into sleeve 45 to remove the clot debris coating flexible shaft 12. These functions can be accomplished by uncoupled co-axial motion of sleeve 45 over flexible shaft 12 concurrent or not to rotation of these elements along their main axis. Uncoupled motion can be optionally done, for example, with discrete notches or a continuous distance adjustment mechanism, with or without a spring system.

In some embodiments, sleeve 45, catheter 14, and/or flexible shaft 12 can have features to enhance clot debris stripping from flexible shaft 12, such as cutting edges or ridges, tight tolerance, elastic recoil, reinforcement bands, and chip breakers.

In other embodiment, sleeve 45 can be used as a channel to actively or passively infuse solutions from fluid port 49 (for example, medications, physiological fluids, lubricious solutions, cooling solutions) or aspirate before, during, or after the thrombectomy.

Method

Figure 17A:
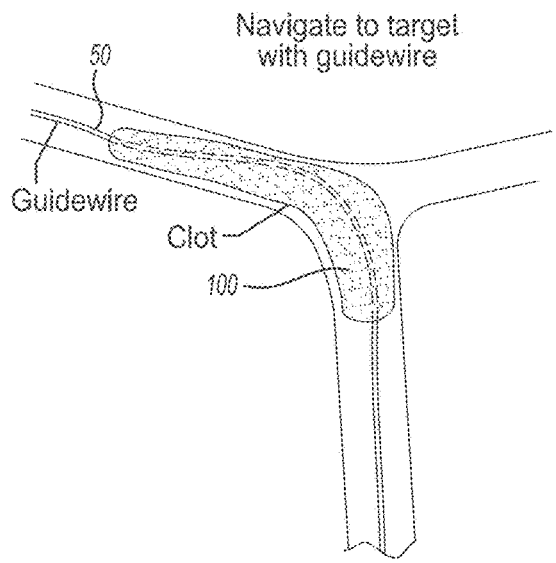
Figure 17B:
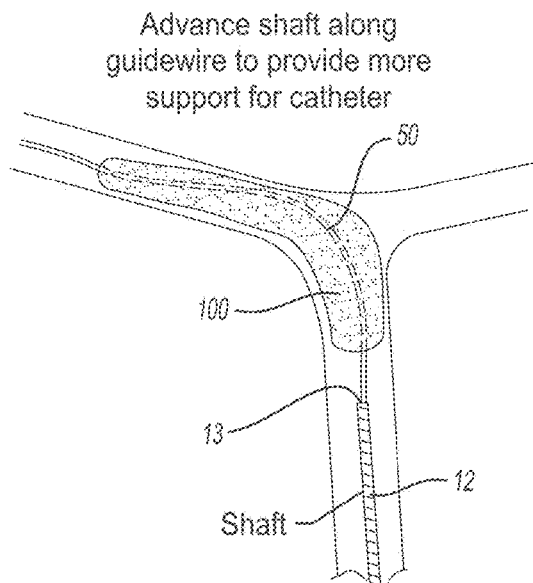
Figure 17C:
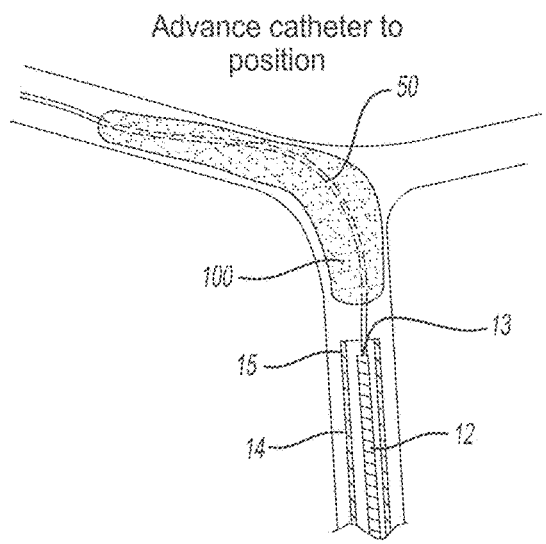
Figure 17D:
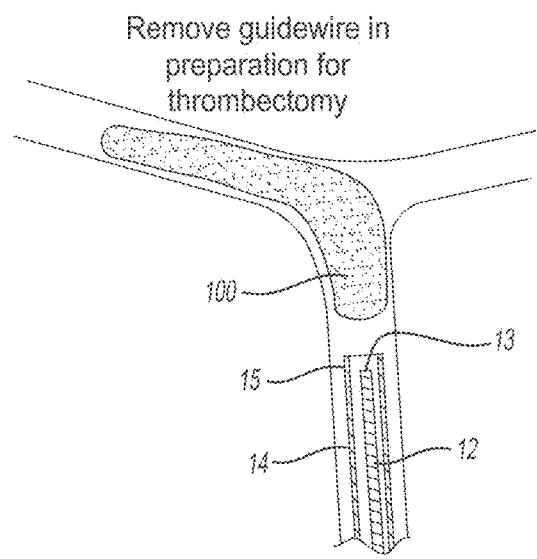
Figure 20A:
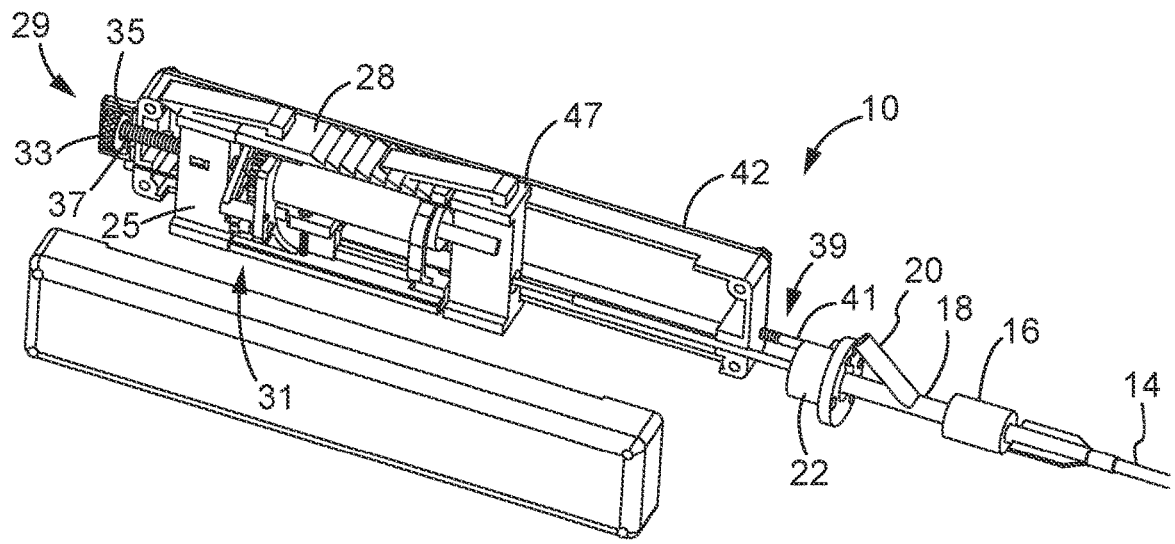
FIG. 20A is an exploded perspective view illustrating an aspiration catheter system according to the principles of the present teachings having a sleeve and sleeve slider in a retracted position.
Figure 20B:
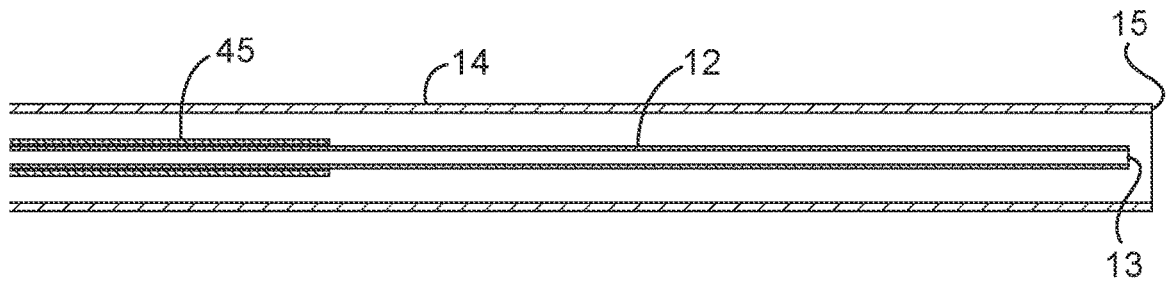
FIG. 20B is a partial cross-sectional view of the catheter, the sleeve, and the flexible shaft in the retracted position of FIG. 20A.
Figure 21A:
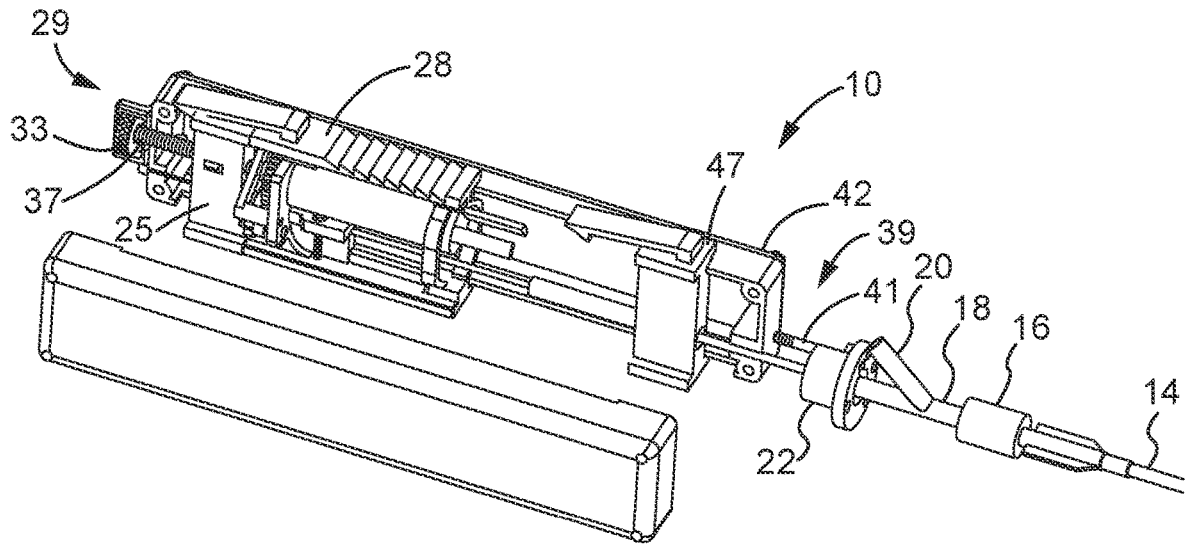
FIG. 21A is an exploded perspective view illustrating the aspiration catheter system of FIG. 20A according to the principles of the present teachings having the sleeve and guidewire in an extended position.
Figure 21B:
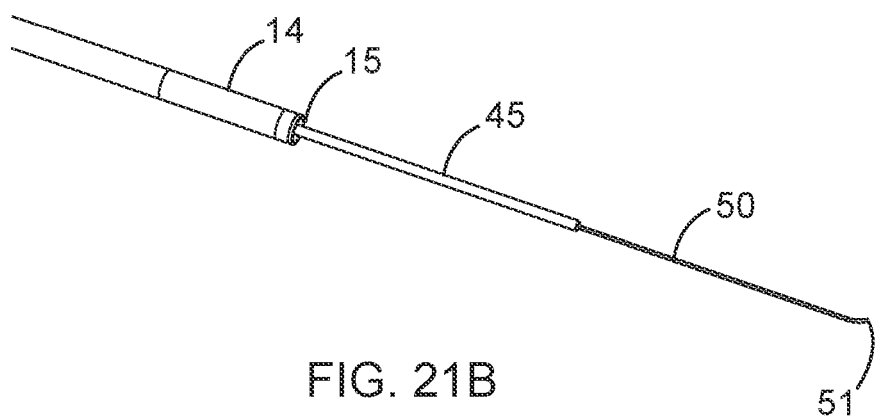
FIG. 21B is a partial perspective view of the catheter, the sleeve, and the guidewire in the extended position of FIG. 21A.
Figure 22A:
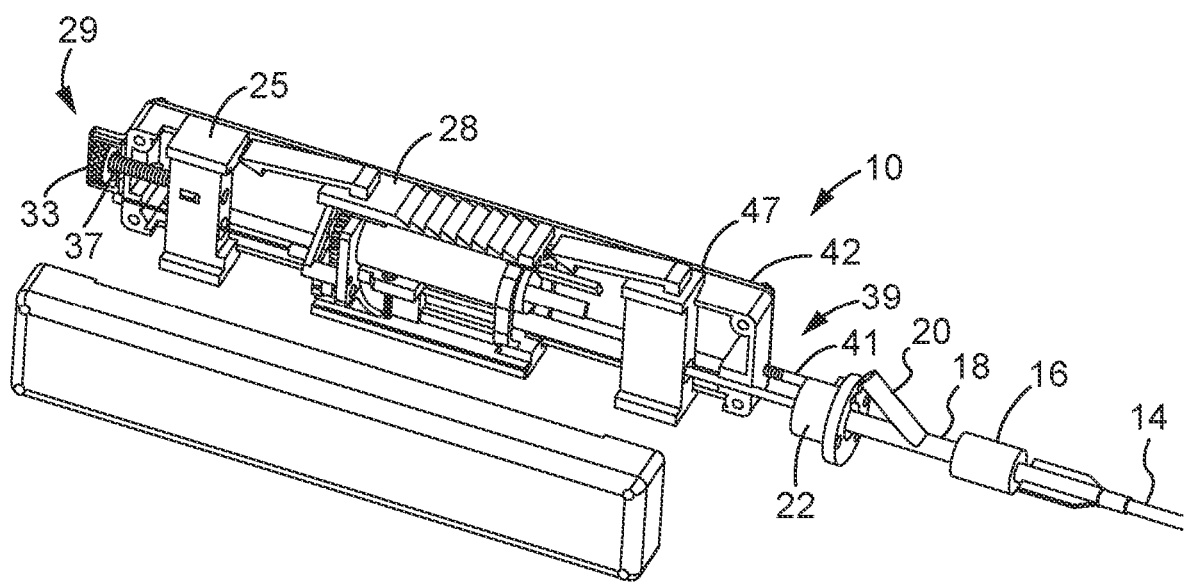
FIG. 22A is an exploded perspective view illustrating the aspiration catheter system of FIG. 20A according to the principles of the present teachings having the sleeve, the flexible shaft, and guidewire in an extended position.
Figure 22B:
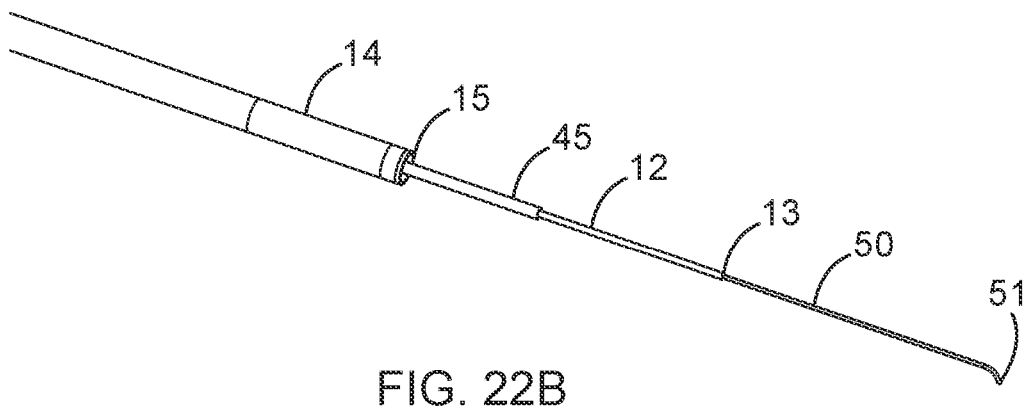
FIG. 22B is a partial perspective view of the catheter, the sleeve, the flexible shaft, and the guidewire in the extended position of FIG. 22A.

With reference to FIGS. 17A-17G, in some embodiments during clot maceration and removal, guidewire 50 is advanced within the lumen of the vessel/cavity/space to clot 100 (FIG. 17A). Distal end 13 of flexible shaft 12 is then advanced along guidewire 50 and placed in proximity, within or passed the mass of clot 100 (FIG. 17B). The longitudinal displacement of the shaft 12 can be facilitated by low speed rotation, oscillation, or vibration by the dive system 32. Distal end 15 of catheter 14 is then navigated into the target vessel/cavity/space and placed in proximity, within, or past the mass of clot 100 (FIG. 17C). During this navigation and positioning, it can also be advantageous to retract shaft 12 in cooperation with the advancement of catheter 14. This can be achieved through manual or automatic retraction actuation of shaft advancement slider 28 in cooperation with manual or automatic advancement of catheter 14 by means of vacuum port assembly 18 and/or aspiration catheter system 10. In some embodiments, catheter 14 can be further supported internally and/or externally using additional supporting elements such as a guiding catheter, an introducer, sleeve 45, or combinations thereof. Guidewire 50 can be retracted or fully removed from the vessel or aspiration catheter system 10. Flexible shaft 12 is positioned in catheter 14 to reach maximal thrombectomy zone 74 (FIG. 17D). Suction from vacuum source 24 begins and draws clot 100 portion into clot engager zone 70 of catheter 14 either prior, concurrent and/or after the flexible shaft 12 is rotated at high speed in accordance with the principles of the present teachings. Thrombectomy is fully contained within catheter 14 as described herein. Catheter 14 and clot 100 remain engaged during the thrombectomy stage (FIGS. 17E-17G and 19A-19G). Suction continues and clot 100 enters further into maximal thrombectomy zone 74 of catheter 14. Flexible shaft 12 is further rotated inside catheter 14 at high speed generating thrombectomy by the mechanisms described herein. However, as needed during the thrombectomy procedure, the rotation of flexible shaft 12 can be momentarily stopped and once again become the navigation and scaffolding element if needed. The fragmented clot 100 inside catheter 14 is continuously aspirated away from the vascular lumen and undergoes further fragmentation along the total length of catheter 14 by the mechanisms described herein.

In some embodiments, the relative distance between flexible shaft 12 and catheter 14 can be adjusted by the shaft adjustment device 25 and/or the momentary adjustment system 29, and/or catheter adjustment device 39 before, during, or after the thrombectomy under X-ray guidance.

In some embodiments, fragmentation and/or maceration of clot 100 are only active in maximal thrombectomy zone 74 (FIGS. 17E-17G). Simultaneously, un-fragmented clot 100 is dragged inwards into clot engager zone 70 and then further into maximal thrombectomy zone 74 for further thrombectomy as described herein.

In some embodiments, the action of thrombectomy and maceration in FIGS. 17E-17G results in catheter 14 advancing into the substance of clot 100 and distally into the target vessels until complete removal of clot 100 is achieved (FIG. 17G).

In some embodiments, catheter 14 can be navigated within or passing the clot mass and then receded during thrombectomy until complete removal of clot 100 is achieved.

In some embodiments, sleeve 45 can be advanced at least partially over flexible shaft 12 to facilitate advancement of catheter 14 to target, and then at least partially withdrawn to enable the generation of thrombectomy forces between flexible shaft 12 and catheter 14.

In some embodiments, as illustrated in FIGS. 18A-18D, a secondary wire 99 can be used to guide catheter 14 and flexible shaft 12 during thrombectomy. The secondary wire 99 can be located in channel 52 of catheter 14 or along a channel thereof.

In some embodiments, flexible shaft 12 can be actuated at or near the proximal end of flexible shaft 12 to induce translational motion at least at the distal end of catheter 14. This can be used both exclusively and in conjunction with the rotational motion to increase thrombectomy capability.

In some embodiments, shaft 12 can be rotated at high speed outside (e.g. beyond) distal end 15 of catheter 14 following orbital movements that extend along a path that can be larger than the diameter of catheter 14. The diameter of this orbital movement of shaft 12 outside catheter 14 is dependent upon the rotational speed, the length of shaft 12 protruding outside catheter 14, the ID of catheter 14, and the flexibility of shaft 12. The translational movement of a shaft 12 with enough stiffness to act as cutting tool will generate a cutting cone to fragment tissues and clots 100. This can be coupled with vacuum to removed fragmented debris. This can be coupled by a bipolar mechanism (between an electrified shaft or shaft tip and catheter 14 distal-most opening) to induce bipolar current and simultaneous coagulation during tissue maceration. This can also be coupled to hollow channel 52 along the wall of catheter 14 that enables a fluid media to be delivered at or near the distal end of catheter 14 which can then backfill the lumen of catheter 14 via vacuum. This would enable the generation of hydraulic forces and translational shaft motions when catheter 14 is not already immersed into a liquid environment.

In some embodiments, the method for removing undesirable material from within a vessel can comprise obtaining endovascular access percutaneously or by cut down and introducing a sheath. The thrombectomy system is then introduced through the sheath into the endovascular space. The guidewire 50 or the secondary wire 99 is advanced to the clot 100 and the flexible shaft 12 is advanced to the clot. In some embodiments, the flexible shaft 12 is advanced over the guidewire 50. The catheter 14 is then advanced over the flexible shaft 12 and/or guidewire 50 to the clot 100. The guidewire 50 can then be removed partially or totally. The catheter 14 and/or flexible shaft 12 is then positioned such that the flexible shaft 12 is fully contained within the catheter 14. Vacuum is then provided to the aspiration catheter system. The thrombectomy mechanism is the activated while the catheter is stationary or moving longitudinally in the vascular lumen. If secondary wire 99 is used, the catheter is moved longitudinally over the secondary wire 99 while thrombectomy mechanism is active. If proximal occlusion mechanism is used: inflate balloon, then activate thrombectomy. If distal occlusion mechanism is used: inflate balloon, then activate thrombectomy. Distal balloon of filter can be pulled back into catheter before, during, or after the thrombectomy enhancing clot-catheter interaction.

In some embodiments, the completeness of the clot removal can be detected in real time and the operator will be informed to end the thrombectomy mode in time to minimize blood loss related to the continuation of vacuum after vessel recanalization. This can be achieved by: 1) sensing the pressure inside the proximal portion of catheter 14, the telescoping system, the actuator handle, the connecting cord between the vacuum pump and the catheter, and/or the vacuum pump 24, as the pressure inside the aforementioned parts will be of the lowest value the distal end 15 of catheter 14 is engaged and blocked by the clot 100 (maximum vacuum generation) and will increase upon the vascular recanalization with aspiration of blood through the catheter 14 (vacuum drop); 2) the torque and force on flexible shaft 12, as flexible shaft 12 will experience cutting, friction, contacting forces and torques while macerating and interacting with the clot 100 and clot fragments and the force and torque on flexible shaft 12 will drop upon the complete removal of the clot 100; 3) the power draw for shaft actuation, as flexible shaft 12 actuation power is positively correlated with the force and torque on flexible shaft 12 and will drop upon the complete clot removal; 4) the power draw from the vacuum pump 24, as the vacuum pump 24 will consume a higher power when generating a lower pressure in catheter 14 due to the catheter distal tip block and engagement with clot, and the vacuum pump 24 power draw will drop when pressure increases upon clot removal and blood aspiration through the catheter; 5) the electric current in shaft actuation and vacuum pump, as the current is positively correlated with the aforementioned power draw; 6) the acoustic frequency and magnitude produced by the system, as the operational sound of flexible shaft 12 actuation system and vacuum pump will change at different power consumption; and 7) the visual feedback provided to the operator upon the identification of blood aspirated into the canister. Upon detection of the complete clot removal, audio, visual, or haptic feedback can be provided to the operator.

In some embodiments, jamming or stalling of flexible shaft 12 and components of the telescoping system can be monitored in real time by: 1) the torque and force on flexible shaft 12, as these will increase significantly and sharply upon jamming or stalling; 2) the power draw for shaft actuation, as the power draw is positively correlated with flexible shaft 12 force and torque which will increase upon jamming or stalling; and 3) the electric current in shaft actuation system, as the current is one of the measures for power draw which is positively correlated with power draw and will increase upon jamming or stalling. Upon the detection of the catheter jam/shaft stall, the thrombectomy mechanism will be automatically stopped and audio, visual, or haptic feedback will be provided to the operator. The response to catheter jam/shaft stall can be implemented via mechanical mechanism and electronic control or the combination of both. The mechanical mechanism to automatically stop the thrombectomy upon detection of the catheter jam or shaft stall includes but not limited to a torque limited coupling.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An apparatus, comprising:
an aspiration catheter defining a lumen, the aspiration catheter configured to be coupled to a vacuum source that can apply a vacuum pressure within the lumen, the aspiration catheter including a distal end configured to be disposed within a vessel near a thrombus;
a flexible shaft configured to be disposed within the lumen, the flexible shaft having a bending stiffness that is greater at a proximal end of the flexible shaft and is reduced at a distal end of the flexible shaft, the flexible shaft including an eccentric mass embedded within the flexible shaft at or near the distal end of the flexible shaft;
a drive system configured to be coupled to the flexible shaft, the drive system configured to translate the flexible shaft relative to the aspiration catheter, the drive system further configured to rotate the flexible shaft when the distal end of the flexible shaft is disposed within the lumen such that the distal end of the flexible shaft can reshape the thrombus to enable the thrombus to be drawn proximally within the lumen, the flexible shaft having sufficient torsional strength to resist breakage when rotated by the drive system,
when the flexible shaft is rotated by the drive system, the distal end of the flexible shaft rotating about a longitudinal axis of the flexible shaft and moving orbitally about a longitudinal axis of the aspiration catheter to reshape and draw the thrombus into the lumen, the eccentric mass configured to enhance the orbital movement of the distal end of the flexible shaft when the drive system rotates the flexible shaft; and a set of one or more seals configured to be disposed within or about the drive system, the set of one or more seals configured to prevent leakage of vacuum pressure applied within the lumen.

2. The apparatus of claim 1, wherein the bending stiffness of the proximal end of the flexible shaft is less than 5000 N·mm², and the bending stiffness of the distal end of the flexible shaft is less than 50 N·mm².

3. The apparatus of claim 1, wherein the flexible shaft has sufficient torsional strength to resist breakage when rotated by the drive system at a speed greater than 10,000 revolutions per minute (RPM).

4. The apparatus of claim 1, wherein the flexible shaft is formed of a plurality of segments, each segment from the plurality of segments having a different bending stiffness with more distal segments having a lower bending stiffness than more proximal segments.

5. An apparatus, comprising:
an aspiration catheter defining a lumen, the aspiration catheter configured to be coupled to a vacuum source that can apply a vacuum pressure within the lumen, the aspiration catheter including a distal end configured to be disposed within a vessel near a thrombus;
a flexible shaft configured to be disposed within the lumen, the flexible shaft transitionable between a first configuration for navigating the distal end of the aspiration catheter to the thrombus and a second configuration for reshaping the thrombus, the flexible shaft in the first configuration having a distal end of the flexible shaft disposed distal to the distal end of the aspiration catheter, the flexible shaft in the second configuration having the distal end of the flexible shaft disposed proximal to the distal end of the aspiration catheter, the flexible shaft including an eccentric mass embedded within the flexible shaft at or near the distal end of the flexible shaft; and
a drive system configured to be coupled to the flexible shaft, the drive system configured to translate the flexible shaft relative to the aspiration catheter to move the flexible shaft between the first configuration and the second configuration, the drive system further configured to rotate the flexible shaft in the second configuration to enable the thrombus to be drawn proximally within the lumen,
when the flexible shaft is rotated by the drive system, the distal end of the flexible shaft rotating about a longitudinal axis of the flexible shaft and moving orbitally about a longitudinal axis of the aspiration catheter to reshape and draw the thrombus into the lumen, the eccentric mass configured to enhance the orbital movement of the distal end of the flexible shaft when the drive system rotates the flexible shaft.

6. The apparatus of claim 5, wherein the drive system is configured to rotate the flexible shaft in the second configuration at a speed greater than 10,000 revolutions per minute (RPM).

7. The apparatus of claim 6, wherein the drive system is configured to rotate the flexible shaft in the first configuration at a speed of less than 200 revolutions per minute (RPM).

8. An apparatus, comprising:
an aspiration catheter defining a first lumen, the aspiration catheter configured to be coupled to a vacuum source that can apply a vacuum pressure within the first lumen, the aspiration catheter including a distal end configured to be disposed within a vessel near a thrombus;
a flexible shaft configured to be disposed within the first lumen, the flexible shaft having a proximal end, a distal end, and a second lumen extending from the proximal end to the distal end, the second lumen configured to receive a guidewire, the flexible shaft having a diameter that decreases or remains constant from the proximal end to the distal end of the flexible shaft, the flexible shaft including an eccentric mass embedded within the flexible shaft at or near the distal end of the flexible shaft;
a drive system configured to be coupled to the flexible shaft, the drive system configured to translate the flexible shaft relative to the aspiration catheter, the drive system further configured to rotate the flexible shaft when the distal end of the flexible shaft is disposed within the first lumen,
when the flexible shaft is rotated by the drive system, the distal end of the flexible shaft rotating about a longitudinal axis of the flexible shaft and moving orbitally about a longitudinal axis of the aspiration catheter to reshape and draw the thrombus into the first lumen, the eccentric mass configured to enhance the orbital movement of the distal end of the flexible shaft when the drive system rotates the flexible shaft; and
a set of one or more seals configured to be disposed within or about the drive system, the set of one or more seals configured to prevent leakage of vacuum pressure applied within the first lumen.

9. The apparatus of claim 8, wherein the proximal end of the flexible shaft has an outer diameter that is greater than the outer diameter of the distal end of the flexible shaft.

10. The apparatus of claim 9, wherein the outer diameter of the proximal end of the flexible shaft is between 0.026 inches and 0.040 inches, and the outer diameter of the distal end of the flexible shaft is between 0.026 inches and 0.034 inches.

11. The apparatus of claim 8, wherein the rotation and the orbital movement of the distal end of the flexible shaft further enhances proximal movement of the thrombus within the first lumen by transforming static friction between the thrombus and an inner wall of the aspiration catheter to kinetic friction.

12. The apparatus of claim 8, wherein the flexible shaft is transitionable from a linear configuration into a non-linear configuration in which a distal end of the flexible shaft has at least one of an angle or a non-linear shape.

13. The apparatus of claim 12, wherein the flexible shaft is transitionable from the linear configuration into the non-linear configuration after a guidewire received within the second lumen of the flexible shaft has been removed from the second lumen of the flexible shaft.

14. The apparatus of claim 8, wherein the flexible shaft is formed from multiple layers of wound wires.

15. The apparatus of claim 8, wherein the flexible shaft is formed from wires wound in opposite directions.

16. The apparatus of claim 8, wherein the flexible shaft is formed of a plurality of segments, each segment from the plurality of segments having a different stiffness with more distal segments having a lower stiffness than more proximal segments.

17. The apparatus of claim 16, wherein the each segment from the plurality of segments further has a different diameter with more distal segments having a smaller diameter than more proximal segments.

18. The apparatus of claim 16, wherein the plurality of segments includes more than two segments.

19. The apparatus of claim 8, wherein the rotation and the orbital movement of the distal end of the flexible shaft generates a pressure difference from outside to inside the first lumen of the aspiration catheter to draw the thrombus into the first lumen.

20. An apparatus, comprising:
  an aspiration catheter defining a first lumen, the aspiration catheter configured to be coupled to a vacuum source that can apply a vacuum pressure within the first lumen, the aspiration catheter including a distal end configured to be disposed within a vessel near a thrombus;
  a flexible shaft configured to be disposed within the first lumen, the flexible shaft having a proximal end, a distal end, and a second lumen extending from the proximal end to the distal end, the second lumen configured to receive a guidewire, the flexible shaft having a diameter that decreases or remains constant from the proximal end to the distal end of the flexible shaft, the flexible shaft transitionable from a linear configuration into a non-linear configuration in which the distal end of the flexible shaft has at least one of an angle or a non-linear shape, the flexible shaft being transitionable from the linear configuration into the non-linear configuration after a guidewire received within the second lumen of the flexible shaft has been removed from the second lumen of the flexible shaft;
  a drive system configured to be coupled to the flexible shaft, the drive system configured to translate the flexible shaft relative to the aspiration catheter, the drive system further configured to rotate the flexible shaft when the distal end of the flexible shaft is disposed within the first lumen,
  when the flexible shaft is rotated by the drive system, the distal end of the flexible shaft rotating about a longitudinal axis of the flexible shaft and moving orbitally about a longitudinal axis of the aspiration catheter to reshape and draw the thrombus into the first lumen; and
  a set of one or more seals disposable within or about the drive system, the set of one or more seals configured to prevent leakage of vacuum pressure applied within the first lumen.

21. The apparatus of claim 20, wherein a bending stiffness of the proximal end of the flexible shaft is less than 5000 N·mm$^2$, and a bending stiffness of the distal end of the flexible shaft is less than 50 N·mm$^2$.

22. The apparatus of claim 20, wherein the flexible shaft has sufficient torsional strength to resist breakage when rotated by the drive system at a speed greater than 10,000 revolutions per minute (RPM).

23. The apparatus of claim 20, wherein the flexible shaft is formed of a plurality of segments, each segment from the plurality of segments having a different bending stiffness with more distal segments having a lower bending stiffness than more proximal segments.

24. The apparatus of claim 20, wherein the drive system is configured to rotate the flexible shaft in the non-linear configuration at a speed greater than 10,000 revolutions per minute (RPM).

25. The apparatus of claim 20, wherein the drive system is configured to rotate the flexible shaft in the linear configuration at a speed of less than 200 revolutions per minute (RPM).

26. The apparatus of claim 20, wherein the proximal end of the flexible shaft has an outer diameter that is greater than an outer diameter of the distal end of the flexible shaft.

27. The apparatus of claim 20, wherein an outer diameter of the proximal end of the flexible shaft is between 0.026 inches and 0.040 inches, and an outer diameter of the distal end of the flexible shaft is between 0.026 inches and 0.034 inches.

28. The apparatus of claim 20, wherein the rotation and the orbital movement of the distal end of the flexible shaft further enhances proximal movement of the thrombus within the first lumen by transforming static friction between the thrombus and an inner wall of the aspiration catheter to kinetic friction.

29. The apparatus of claim 20, wherein the rotation and the orbital movement of the distal end of the flexible shaft generates a pressure difference from outside to inside the first lumen of the aspiration catheter to draw the thrombus into the first lumen.

30. The apparatus of claim 20, wherein the flexible shaft is formed from multiple layers of wound wires.

* * * * *